US009079951B2

(12) United States Patent
Chevreux et al.

(10) Patent No.: US 9,079,951 B2
(45) Date of Patent: Jul. 14, 2015

(54) METHOD FOR PRODUCTION OF VITAMIN C

(75) Inventors: Bastien Chevreux, Rheinfelden (DE); Corina Hauk, Weil am Rhein (DE); Andrea Muffler, Bad Saeckingen (DE); Nigel J. Mouncey, Binningen (CH); Masako Shinjoh, Kanagawa (JP)

(73) Assignee: DSM IP ASSETS B.V., Heerlen (NL)

( * ) Notice: Subject to any disclaimer, the term of this patent is extended or adjusted under 35 U.S.C. 154(b) by 435 days.

(21) Appl. No.: 12/905,282

(22) Filed: Oct. 15, 2010

(65) Prior Publication Data

US 2011/0039310 A1 Feb. 17, 2011

Related U.S. Application Data

(63) Continuation of application No. 11/991,399, filed as application No. PCT/EP2006/008706 on Sep. 7, 2006, now abandoned.

(30) Foreign Application Priority Data

Sep. 8, 2005 (EP) .................................... 05021368

(51) Int. Cl.

| | |
|---|---|
| ***C12P 17/04*** | (2006.01) |
| ***C12N 1/21*** | (2006.01) |
| ***C12N 15/63*** | (2006.01) |
| ***C12N 15/74*** | (2006.01) |
| ***C07K 14/195*** | (2006.01) |

(52) U.S. Cl.

CPC ............... *C07K 14/195* (2013.01); *C12P 17/04* (2013.01)

(58) Field of Classification Search

CPC ............ C12P 17/04; C12P 7/60; C12P 17/00; C12P 7/24; C12P 7/26; C12P 7/40; C12N 9/0006; C12N 9/0008; C12N 9/1223; C12N 9/0004; C12N 9/0053; C12N 15/102; C12N 15/52

USPC ............. 435/252.3, 320.1, 252.33, 126, 243, 435/252.34, 471, 105, 52.32, 472, 138, 144, 435/254.2, 83, 69.1; 536/23.1, 23.7, 24.1; 530/350, 300, 324

See application file for complete search history.

(56) References Cited

U.S. PATENT DOCUMENTS

2008/0274520 A1 11/2008 Chevreux et al.

FOREIGN PATENT DOCUMENTS

| | | |
|---|---|---|
| WO | 2004/029235 | 4/2004 |
| WO | 2004/029268 | 4/2004 |
| WO | 2006/084714 | 8/2006 |

OTHER PUBLICATIONS

Macaukey et al Critical reviews in Biotechnology, 2001, 21, 1-25.*
Bowie, et al. (Science, 247: 1306-10, 1990.*
Skolnick et al. TIBTECH 18:34-39, 2000.*
Prust et al Nature Biotechnology, 2005, 23, 193-200.*
Rychlik et al. Nuc. Acids Res. 18:6409-6412, 1990.*
Deppenmeier et al., "Biochemistry and biotechnological applications of *Gluconobacter* strains" *Applied Microbiology and Biotechnology*, vol. 60, No. 3, pp. 233-242 (Nov. 2002).
Macauley et al., "The genus*Gluconobacter* and its applications in biotechnology" *CRC Critical Reviews in Biotechnology*, vol. 21, No. 1, pp. 1-25 (2001).
Prust et al., "Complete genome sequence of the acetic acid bacterium *Gluconobacter oxydans" Nature Biotechnology*, vol. 23, No. 2, pp. 195-200 (Feb. 2005).
Int'l Search Report for PCT/EP2006/008706 completed Nov. 28, 2006.
Bowie et al, "Deciphering the Message in Protein Sequences: Tolerance to Amino Acid Substitutions", Science, 1990, 247:1306-10.
Rychlik et al, "Optimization of the annealing temperature for DNA amplification in vitro", Nuc. Acids Res. 1990, 18:6409-6412.
Skolnick et al, "From genes to protein structure and function: novel applications of computational approaches in the genomic era", TIBTECH 18:34-39, 2000.
Saito et al, "Direct Fermentation of 2-Keto-L-Gulonic Acid in Recombinant *Gluconobacter oxydans*", Biotechnology and Bioengineering, 1998, 58, 309-315.

* cited by examiner

*Primary Examiner* — Anoop Singh
(74) *Attorney, Agent, or Firm* — Nixon & Vanderhye P.C.

(57) ABSTRACT

The present invention relates to newly identified genes that encode proteins that are involved in the synthesis of L-ascorbic acid (hereinafter also referred to as Vitamin C). The invention also features polynucleotides comprising the full-length polynucleotide sequences of the novel genes and fragments thereof, the novel polypeptides encoded by the polynucleotides and fragments thereof, as well as their functional equivalents. The present invention also relates to the use of the polynucleotides and polypeptides as biotechnological tools in the production of Vitamin C from microorganisms, whereby a modification of the polynucleotides and/or encoded polypeptides has a direct or indirect impact on yield, production, and/or efficiency of production of the fermentation product in the microorganism. Also included are methods/processes of using the polynucleotides and modified polynucleotide sequences to transform host microorganisms. The invention also relates to genetically engineered microorganisms and their use for the direct production of Vitamin C.

4 Claims, No Drawings

SEQUENCE LISTING

```
<160> NUMBER OF SEQ ID NOS: 10

<210> SEQ ID NO 1
<211> LENGTH: 1401
<212> TYPE: DNA
<213> ORGANISM: Gluconobacter oxydans DSM 17078
```

<400> SEQUENCE: 1

```
atgagtgacg ttggcgtcgt agagagcgtt ccgcgcgttt cactcaacgg cagaagtgcc     60

ctggtagcca ctctggctgc ggtggcaggt ctgatgttcg ggctggatct gggtgtcata    120

tccggagcgc tgaaattcat cggtatcgag tttcaggtca atgatttcgg caaggagtgc    180

attgtctccg gcatgatggt cggagcagcg ctcggggccc tgttcggtgg gcggctgtcc    240

tatattctgg ggcgcaaaaa gctgctgatc atctcggcac tgctcttcat ttccgggtcg    300

gcactctgcg cgctggcacc ctccgttccg gtcctgatcg cggggcgtgt ggtccttgga    360

ctggcgatcg gcgtcgcgag ctttaccgct ccactctata tttcggagat tgcgcaccag    420

cagcatcgcg gggcgctgat ttccgtctat cagctcatga ttacggtggg cattctggtc    480

gcgttcatct ccgatgcgct tctggcctat tcgggatcat ggcgctggat gctggggatc    540

gtgggtgtcc ccggcgtgct gttcctgatc ggtgtcctgt tccttccgga cagcccgcgc    600

tggctggttc tgcgggggcg gcatgatgaa gcgttcgatg tcctgcacgg gctgcgtggc    660

aatgatgcgc atgcgcggga cgagatcgtc gaaatccgtg atcagcttgc acaggccgat    720

ggcggatata cgctcttcaa gaaaaacccg aacttccgcc gcgcggtcta tctgggcgtg    780

gcgcttcagg cgatccagca gttcaccggc atcaacgtgg tcatgtacta cgcgccgcat    840

atcttcgaaa tggccggttt cggcaccagt gccgccctgt ggggcacggt gatcgtggga    900

ctggtcaatg tgctctccac gttcatcgcc attggatatg tcgatcgctg gggccggcgg    960

cccatgctga tcgcgggctt catcatgatg gcgctcggta tgtttacggt cggcatgctg   1020

atgtatttcg gcacgggcaa cagcgatctg gcgcgttacg cggcagttgc gatgctgctg   1080

tgcttcatcg tcgggtttgc attttccgcc gggccgctgg tgtggatcct gtgctctgaa   1140

gttcagccca tgaaggggcg tgacttcggc atcgggtgct cgaccttcac caactggggc   1200

accaacatga ttgttggtct gaccttcctc tcgcttctga cgacactggg aagtgcccag   1260

accttctggc tctatgccct gcttaatctc atcttcattt tcgtgacgat gaagttcgtg   1320

ccggaaaccc gtggcgtgtc gcttgagcag atcgagcgga atctcatggc cggtaaaccc   1380

ctcaatcgta tcggcctgta a                                             1401
```

<210> SEQ ID NO 2
<211> LENGTH: 466
<212> TYPE: PRT
<213> ORGANISM: Gluconobacter oxydans DSM 17078

<400> SEQUENCE: 2

```
Met Ser Asp Val Gly Val Val Glu Ser Val Pro Arg Val Ser Leu Asn
1               5                   10                  15

Gly Arg Ser Ala Leu Val Ala Thr Leu Ala Ala Val Ala Gly Leu Met
            20                  25                  30

Phe Gly Leu Asp Leu Gly Val Ile Ser Gly Ala Leu Lys Phe Ile Gly
        35                  40                  45

Ile Glu Phe Gln Val Asn Asp Phe Gly Lys Glu Cys Ile Val Ser Gly
    50                  55                  60

Met Met Val Gly Ala Ala Leu Gly Ala Leu Phe Gly Gly Arg Leu Ser
65                  70                  75                  80

Tyr Ile Leu Gly Arg Lys Lys Leu Leu Ile Ile Ser Ala Leu Leu Phe
                85                  90                  95

Ile Ser Gly Ser Ala Leu Cys Ala Leu Ala Pro Ser Val Pro Val Leu
            100                 105                 110
```

-continued

```
Ile Ala Gly Arg Val Val Leu Gly Leu Ala Ile Gly Val Ala Ser Phe
        115                 120                 125

Thr Ala Pro Leu Tyr Ile Ser Glu Ile Ala His Gln Gln His Arg Gly
    130                 135                 140

Ala Leu Ile Ser Val Tyr Gln Leu Met Ile Thr Val Gly Ile Leu Val
145                 150                 155                 160

Ala Phe Ile Ser Asp Ala Leu Leu Ala Tyr Ser Gly Ser Trp Arg Trp
                165                 170                 175

Met Leu Gly Ile Val Gly Val Pro Gly Val Leu Phe Leu Ile Gly Val
            180                 185                 190

Leu Phe Leu Pro Asp Ser Pro Arg Trp Leu Val Leu Arg Gly Arg His
        195                 200                 205

Asp Glu Ala Phe Asp Val Leu His Gly Leu Arg Gly Asn Asp Ala His
    210                 215                 220

Ala Arg Asp Glu Ile Val Glu Ile Arg Asp Gln Leu Ala Gln Ala Asp
225                 230                 235                 240

Gly Gly Tyr Thr Leu Phe Lys Lys Asn Pro Asn Phe Arg Arg Ala Val
                245                 250                 255

Tyr Leu Gly Val Ala Leu Gln Ala Ile Gln Gln Phe Thr Gly Ile Asn
            260                 265                 270

Val Val Met Tyr Tyr Ala Pro His Ile Phe Glu Met Ala Gly Phe Gly
        275                 280                 285

Thr Ser Ala Ala Leu Trp Gly Thr Val Ile Val Gly Leu Val Asn Val
    290                 295                 300

Leu Ser Thr Phe Ile Ala Ile Gly Tyr Val Asp Arg Trp Gly Arg Arg
305                 310                 315                 320

Pro Met Leu Ile Ala Gly Phe Ile Met Met Ala Leu Gly Met Phe Thr
                325                 330                 335

Val Gly Met Leu Met Tyr Phe Gly Thr Gly Asn Ser Asp Leu Ala Arg
            340                 345                 350

Tyr Ala Ala Val Ala Met Leu Leu Cys Phe Ile Val Gly Phe Ala Phe
        355                 360                 365

Ser Ala Gly Pro Leu Val Trp Ile Leu Cys Ser Glu Val Gln Pro Met
    370                 375                 380

Lys Gly Arg Asp Phe Gly Ile Gly Cys Ser Thr Phe Thr Asn Trp Gly
385                 390                 395                 400

Thr Asn Met Ile Val Gly Leu Thr Phe Leu Ser Leu Leu Thr Thr Leu
                405                 410                 415

Gly Ser Ala Gln Thr Phe Trp Leu Tyr Ala Leu Leu Asn Leu Ile Phe
            420                 425                 430

Ile Phe Val Thr Met Lys Phe Val Pro Glu Thr Arg Gly Val Ser Leu
        435                 440                 445

Glu Gln Ile Glu Arg Asn Leu Met Ala Gly Lys Pro Leu Asn Arg Ile
    450                 455                 460

Gly Leu
465
```

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
atgagtgacg ttggcgtcgt 20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ttacaggccg atacgattga 20

<210> SEQ ID NO 5
<211> LENGTH: 42
<212> TYPE: DNA
<213> ORGANISM: Artificial Sequence
<220> FEATURE:
<223> OTHER INFORMATION: primer

<400> SEQUENCE: 5
agttcgcaca ggagttccat atgagtgacg ttggcgtcgt ag 42

<210> SEQ ID NO 6
<211> LENGTH: 400
<212> TYPE: DNA
<213> ORGANISM: Gluconobacter oxydans DSM 17078

<400> SEQUENCE: 6
gtggcctcag cgtccctgac acgctttttc gtagaggagg acgctctgct tttctcaagg 60
ggcatcaggg gtttgttccg ctctcagtag gggcgctctt tctgggggaa accgccccaa 120
aagaaaagcg gatcataaaa tcacacttaa agtacgaaaa aatatcaacg taacgtgatt 180
tcatgctggc gtacccctgc gatatgtgta agtaactaca tggtgcgtta cgcgttagga 240
agttggaacc cgagcgtctg tggtcaaatg caggtgaggg tcgtccgtga ttaagaattg 300
catgttgtaa tatctctcgg ggtttccagt tcataagagt aaaaccgggc tgttcatcgg 360
aaaagggatg gcagcaccat agttcgcaca ggagttcgta 400

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
gagactcgag gtggcctcag cgtccctg 28

<210> SEQ ID NO 8
<211> LENGTH: 42
<212> TYPE: DNA
<213> ORGANISM: Artificial Sequence
<220> FEATURE:
<223> OTHER INFORMATION: primer

<400> SEQUENCE: 8
ctacgacgcc aacgtcactc atatggaact cctgtgcgaa ct 42

<210> SEQ ID NO 9
<211> LENGTH: 495
<212> TYPE: DNA
<213> ORGANISM: Gluconobacter oxydans IFO 3293

<400> SEQUENCE: 9

-continued

```
atgccccttg agaaaagcag agcgtcctcc tctacgaaaa agcgtgtcag ggacgctgag     60

gccacgaaat tacgcattct cgaagcggcg aagaaggagt ttgcccgaaa cgggcttgaa    120

ggcgcgcggg tcgatacgat cgccctcgat gccaaggcca acaagaggat gctctaccac    180

tatttcaaaa gtaaggacgg ccttttccgc accgtcctgg agcgggaata tctcaacatc    240

cgggaggaag agaccagact ggatctggag aacctccccc cccaggacag ccctcgaaac    300

gctcgtccgt ttcacatggg aatactatat cgccaatccg gagttcatca cccttgtgaa    360

cagcgagaac ctctgtcagg ccgcccatat ccggaattca cccacactga agacgatcag    420

tcagaaattc gtccgccgca tccagtccct tctggatcgg ggcgttcggg aaaatgtctt    480

ccgcgatggc attga                                                      495
```

```
<210> SEQ ID NO 10
<211> LENGTH: 164
<212> TYPE: PRT
<213> ORGANISM: Gluconobacter oxydans IFO 3293

<400> SEQUENCE: 10

Met Pro Leu Glu Lys Ser Arg Ala Ser Ser Ser Thr Lys Lys Arg Val
1               5                   10                  15

Arg Asp Ala Glu Ala Thr Lys Leu Arg Ile Leu Glu Ala Ala Lys Lys
            20                  25                  30

Glu Phe Ala Arg Asn Gly Leu Glu Gly Ala Arg Val Asp Thr Ile Ala
        35                  40                  45

Leu Asp Ala Lys Ala Asn Lys Arg Met Leu Tyr His Tyr Phe Lys Ser
    50                  55                  60

Lys Asp Gly Leu Phe Arg Thr Val Leu Glu Arg Glu Tyr Leu Asn Ile
65                  70                  75                  80

Arg Glu Glu Glu Thr Arg Leu Asp Leu Glu Asn Leu Pro Pro Gln Asp
                85                  90                  95

Ser Pro Arg Asn Ala Arg Pro Phe His Met Gly Ile Leu Tyr Arg Gln
            100                 105                 110

Ser Gly Val His His Pro Cys Glu Gln Arg Glu Pro Leu Ser Gly Arg
        115                 120                 125

Pro Tyr Pro Glu Phe Thr His Thr Glu Asp Asp Gln Ser Glu Ile Arg
    130                 135                 140

Pro Pro His Pro Val Pro Ser Gly Ser Gly Arg Ser Gly Lys Cys Leu
145                 150                 155                 160

Pro Arg Trp His
```

METHOD FOR PRODUCTION OF VITAMIN C

This application is a continuation of application Ser. No. 11/991,399 filed Jul. 3, 2008 (published as US2008/0274520-A1 on Nov. 6, 2008) (abandoned), which is the U.S. national phase under 35 USC 371 of International Application No. PCT/EP2006/008706 filed 7 Sep. 2006 which designated the U.S. and claims priority to European Patent Application No. 05021368.5 filed 8 Sep. 2005; the entire contents of each of which are hereby incorporated by reference.

The present invention relates to newly identified genes that encode proteins that are involved in the synthesis of L-ascorbic acid (hereinafter also referred to as Vitamin C). The invention also features polynucleotides comprising the full-length polynucleotide sequences of the novel genes and fragments thereof, the novel polypeptides encoded by the polynucleotides and fragments thereof, as well as their functional equivalents. The present invention also relates to the use of said polynucleotides and polypeptides as biotechnological tools in the production of Vitamin C from microorganisms, whereby a modification of said polynucleotides and/or encoded polypeptides has a direct or indirect impact on yield, production, and/or efficiency of production of the fermentation product in said microorganism. Also included are methods/processes of using the polynucleotides and modified polynucleotide sequences to transform host microorganisms. The invention also relates to genetically engineered microorganisms and their use for the direct production of Vitamin C.

Vitamin C is one of very important and indispensable nutrient factors for human beings. Vitamin C is also used in animal feed even though some farm animals can synthesize it in their own body.

For the past 70 years, Vitamin C has been produced industrially from D-glucose by the well-known Reichstein method. All steps in this process are chemical except for one (the conversion of D-sorbitol to L-sorbose), which is carried out by microbial conversion. Since its initial implementation for industrial production of Vitamin C, several chemical and technical modifications have been used to improve the efficiency of the Reichstein method. Recent developments of Vitamin C production are summarized in Ullmann's Encyclopedia of Industrial Chemistry, 5$^{th}$ Edition, Vol. A27 (1996), pp. 547ff.

Different intermediate steps of Vitamin C production have been performed with the help of microorganisms or enzymes isolated therefrom. Thus, 2-keto-L-gulonic acid (2-KGA), an intermediate compound that can be chemically converted into Vitamin C by means of an alkaline rearrangement reaction, may be produced by a fermentation process starting from L-sorbose or D-sorbitol, by means of strains belonging e.g. to the *Ketogulonicigenium* or *Gluconobacter* genera, or by an alternative fermentation process starting from D-glucose, by means of recombinant strains belonging to the *Gluconobacter* or *Pantoea* genera.

Current chemical production methods for Vitamin C have some undesirable characteristics such as high-energy consumption and use of large quantities of organic and inorganic solvents. Therefore, over the past decades, other approaches to manufacture Vitamin C using microbial conversions, which would be more economical as well as ecological, have been investigated.

Direct Vitamin C production from a number of substrates including D-sorbitol, L-sorbose and L-sorbosone has been reported in several microorganisms, such as algae, yeast and acetic acid bacteria, using different cultivation methods. Examples of known bacteria able to directly produce Vitamin C include, for instance, strains from the genera of *Gluconobacter, Gluconacetobacter, Acetobacter, Ketogulonicigenium, Pantoea, Pseudomonas* or *Escherichia*. Examples of known yeast or algae include, e.g., *Candida, Saccharomyces, Zygosaccharomyces, Schizosaccharomyces, Kluyveromyces* or *Chlorella.*

Microorganisms able to assimilate D-sorbitol for growth usually possess enzymes able to oxidize this compound into a universal assimilation substrate such as D-fructose. Also microorganisms able to grow on L-sorbose possess an enzyme, NAD(P)H-dependent L-sorbose reductase, which is able to reduce this compound to D-sorbitol, which is then further oxidized into D-fructose. D-fructose is an excellent substrate for the growth of many microorganisms, after it has been phosphorylated by means of a D-fructose kinase.

For instance, in the case of acetic acid bacteria, which are obligate aerobe, gram-negative microorganisms belonging to the genus *Acetobacter, Gluconobacter*, and *Gluconacetobacter*, these microorganisms are able to transport D-sorbitol into the cytosol and convert it into D-fructose by means of a cytosolic NAD-dependent D-sorbitol dehydrogenase. Some individual strains, such as *Gluconobacter oxydans* IFO 3292, and IFO 3293, are able as well to transport L-sorbose into the cytosol and reduce it to D-sorbitol by means of a cytosolic NAD(P)H-dependent L-sorbose reductase, which then is further oxidized into D-fructose. In these bacteria, the Embden-Meyerhof-Parnas pathway, as well as the tricarboxyclic acid cycle are not fully active, and the main pathway channeling sugars into the central metabolism is the pentose phosphate pathway. D-fructose-6-phosphate, obtained from D-fructose by a phosphorylation reaction enters the pentose phosphate pathway, being further metabolized and producing reducing power in the form of NAD(P)H and tricarboxylic compounds necessary for growth and maintenance.

Acetic acid bacteria are well known for their ability to incompletely oxidize different substrates such as alcohols, sugars, sugar alcohols and aldehydes. These processes are generally known as oxidative fermentations or incomplete oxidations, and they have been well established for a long time in the food and chemical industry, especially in vinegar and in L-sorbose production. A useful product known to be obtained from incomplete oxidations of D-sorbitol or L-sorbose using strains belonging to the *Gluconobacter* genus is 2-KGA.

Acetic acid bacteria accomplish these incomplete oxidation reactions by means of different dehydrogenases located either in the periplasmic space, on the periplasmic membrane as well as in the cytoplasm. Different co-factors are employed by the different dehydrogenases, the most common being PQQ and FAD for membrane-bound or periplasmic enzymes, and NAD/NADP for cytoplasmic enzymes.

While all products of these oxidation reactions diffuse back to the external aqueous environment through the outer membrane, some of them can be passively or actively transported into the cell and be further used in metabolic pathways responsible for growth and energy formation. Inside the cell, oxidized products can many times be reduced back to their original substrate by means of reductases, and then be channeled back to the central metabolism.

Proteins, in particular enzymes and transporters, that are active in the metabolization of D-sorbitol or L-sorbose are herein referred to as being involved in the Sorbitol/Sorbose Metabolization System. Such proteins are abbreviated herein as SMS proteins and function in the direct metabolization of D-sorbitol or L-sorbose.

Metabolization of D-sorbitol or L-sorbose includes on one side the assimilation of these compounds into the cytosol and further conversion into metabolites useful for assimilation pathways such as the Embden-Meyerhof-Parnas pathway, the pentose phosphate pathway, the Entner-Doudoroff pathway, and the tricarboxylic acid cycle, all of them involved in all vital energy-forming and anabolic reactions necessary for growth and maintenance of living cells. On the other side, metabolization of D-sorbitol or L-sorbose also includes the conversion of these compounds into further oxidized products such as L-sorbosone, 2-KGA and Vitamin C by so-called incomplete oxidation processes.

An object of the present invention is to improve the yields and or productivity of Vitamin C production.

Surprisingly, it has now been found that SMS proteins or subunits of such proteins having activity towards or which are involved in the assimilation Or conversion of D-sorbitol, L-sorbose or L-sorbosone play an important role in the biotechnological production of Vitamin C and/or 2-KGA.

In one embodiment, SMS proteins of the present invention are selected from oxidoreductases [EC 1], preferably oxidoreductases acting on the CH—OH group of donors [EC 1.1], more preferably oxidoreductases with $NAD^+$ or $NADP^+$ as acceptor [EC 1.1.1] and oxidoreductases with other acceptors [EC 1.1.99], most preferably selected from oxidoreductases belonging to enzyme classes [EC 1.1.1.1], [EC 1.1.1.15] or [EC 1.2.1.-], or preferably oxidoreductases acting on the aldehyde or oxo group of donors [EC 1.2], more preferably oxidoreductases with $NAD^+$ or $NADP^+$ as acceptor [EC 1.2.1].

Furthermore, the SMS proteins of the present invention may be selected from the group consisting of membrane-bound PQQ-dependent D-sorbitol dehydrogenase, membrane-bound L-sorbose dehydrogenase, membrane-bound L-sorbosone dehydrogenase, membrane-bound FAD-dependent D-sorbitol dehydrogenase, cytosolic NAD-dependent D-sorbitol dehydrogenase, NAD(P)-dependent D-sorbitol dehydrogenase (also called as NADPH-dependent sorbose reductase), NAD-dependent xylitol dehydrogenase, NAD-dependent alcohol dehydrogenase, membrane-bound L-sorbose dehydrogenase, NAD(P)H-dependent L-sorbose reductase, cytosolic NADP-dependent sorbosone dehydrogenase, cytosolic NAD(P)H-dependent L-sorbosone reductase, membrane-bound aldehyde dehydrogenase, cytosolic aldehyde dehydrogenase, glycerol-3-phosphate dehydrogenase, glyceraldehyde-3-phosphate dehydrogenase, and others involved in SMS including proteins involved in transportation of sugar and/or sugar alcohols in particular symporters, preferably galactose-proton symporter, or exporters of sugar or sugar alcohols, preferably sorbosone exporter.

In particular, it has now been found that SMS proteins encoded by polynucleotides having a nucleotide sequence that hybridizes preferably under highly stringent conditions to a sequence shown in SEQ ID NO:1 play an important role in the biotechnological production of Vitamin C. It has also been found, that by genetically altering the expression level of nucleotides according to the invention in a microorganism capable of directly producing Vitamin C, such as for example *Gluconobacter*, the direct fermentation of Vitamin C by said microorganism can be even greatly improved.

Consequently, the invention relates to a polynucleotide selected from the group consisting of:

(a) polynucleotides encoding a polypeptide comprising the amino acid sequence according to SEQ ID NO:2;
(b) polynucleotides comprising the nucleotide sequence according to SEQ ID NO:1;
(c) polynucleotides comprising a nucleotide sequence obtainable by nucleic acid amplification such as polymerase chain reaction, using genomic DNA from a microorganism as a template and a primer set according to SEQ ID NO:3 and SEQ ID NO:4;
(d) polynucleotides comprising a nucleotide sequence encoding a fragment or derivative of a polypeptide encoded by a polynucleotide of any of (a) to (c) wherein in said derivative one or more amino acid residues are conservatively substituted compared to said polypeptide, and said fragment or derivative has the activity of a sugar exporter and/or sugar alcohol exporter, preferably SMS 37 activity;
(e) polynucleotides the complementary strand of which hybridizes under stringent conditions to a polynucleotide as defined in any one of (a) to (d) and which encode a sugar exporter and/or sugar alcohol exporter, preferably a SMS 37 polypeptide; and
(f) polynucleotides which are at least 60%, such as 70, 85, 90 or 95% identical to a polynucleotide as defined in any one of (a) to (d) and which encode a sugar exporter and/or sugar alcohol exporter, preferably a SMS 37 polypeptide;

or the complementary strand of such a polynucleotide.

The SMS protein as isolated from *Gluconobacter oxydans* DSM 17078 shown in SEQ ID NO:2 and described herein was found to be a particularly useful SMS protein, since it appeared that it performs a crucial function in the direct Vitamin C production in microorganisms, in particular in bacteria, such as acetic acid bacteria, such as *Gluconobacter, Acetobacter* and *Gluconacetobacter*. Accordingly, the invention relates to a polynucleotide encoding a polypeptide according to SEQ ID NO:2. This protein may be encoded by a nucleotide sequence as shown in SEQ ID NO:1. The invention therefore also relates to polynucleotides comprising the nucleotide sequence according to SEQ ID NO:1.

The nucleotide and amino acid sequences determined above were used as a "query sequence" to perform a search with Blast2 program (version 2 or BLAST from National Center for Biotechnology [NCBI] against the database PRO SW-SwissProt (full release plus incremental updates). From the searches, the SMS 37 polynucleotide according to SEQ ID NO:1 was annotated as encoding a protein having galactose-proton symporter activity.

Surprisingly, it has now been furthermore found out that the protein encoded by the SMS 37 polynucleotide according to SEQ ID NO:1 is involved in the export of sugars and/or sugar alcohols, in particular sorbosone. In this connection, "export" means the active transport of a respective compound from the cytoplasm into the periplasm or extracellular environment.

A nucleic acid according to the invention may be obtained by nucleic acid amplification using cDNA, mRNA or alternatively, genomic DNA, as a template and appropriate oligonucleotide primers such as the nucleotide primers according to SEQ ID NO:3 and SEQ ID NO:4 according to standard PCR amplification techniques. The nucleic acid thus amplified may be cloned into an appropriate vector and characterized by DNA sequence analysis.

The template for the reaction may be cDNA obtained by reverse transcription of mRNA prepared from strains known or suspected to comprise a polynucleotide according to the invention. The PCR product may be subcloned and sequenced to ensure that the amplified sequences represent the sequences of a new nucleic acid sequence as described herein, or a functional equivalent thereof.

The PCR fragment may then be used to isolate a full length cDNA clone by a variety of known methods. For example, the amplified fragment may be labeled and used to screen a bacteriophage or cosmid cDNA library. Alternatively, the labeled fragment may be used to screen a genomic library.

Accordingly, the invention relates to polynucleotides comprising a nucleotide sequence obtainable by nucleic acid amplification such as polymerase chain reaction, using DNA such as genomic DNA from a microorganism as a template and a primer set according to SEQ ID NO:3 and SEQ ID NO:4.

The invention also relates to polynucleotides comprising a nucleotide sequence encoding a fragment or derivative of a polypeptide encoded by a polynucleotide as described herein wherein in said derivative one or more amino acid residues are conservatively substituted compared to said polypeptide, and said fragment or derivative has the activity of a SMS polypeptide, preferably a SMS 37 polypeptide.

The invention also relates to polynucleotides the complementary strand of which hybridizes under stringent conditions to a polynucleotide as defined herein and which encode a SMS polypeptide, preferably a SMS 37 polypeptide.

The invention also relates to polynucleotides which are at least 60% identical to a polynucleotide as defined herein and which encode a SMS polypeptide; and the invention also relates to polynucleotides being the complementary strand of a polynucleotide as defined herein above.

The invention also relates to primers, probes and fragments that may be used to amplify or detect a DNA according to the invention and to identify related species or families of microorganisms also carrying such genes.

The present invention also relates to vectors which include polynucleotides of the invention and microorganisms which are genetically engineered with the polynucleotides or said vectors.

The invention also relates to processes for producing microorganisms capable of expressing a polypeptide encoded by the above defined polynucleotide and a polypeptide encoded by a polynucleotide as defined above.

The invention also relates to microorganisms wherein the activity of a SMS polypeptide, preferably a SMS 37 polypeptide, is enhanced and/or improved so that the yield of Vitamin C which is directly produced from D-sorbitol or L-sorbose is increased. This may be accomplished, for example, by transferring a polynucleotide according to the invention into a recombinant or non-recombinant microorganism that may or may not contain an endogenous equivalent of the SMS 37 gene.

The skilled person will know how to enhance and/or improve the activity of a SMS protein, preferably a SMS 37 protein. Such may be for instance accomplished by either genetically modifying the host organism in such a way that it produces more or more stable copies of the SMS protein, preferably the SMS 37 protein, than the wild type organism or by increasing the specific activity of the SMS protein, preferably the SMS 37 protein.

In the following description, procedures are detailed to achieve this goal, i.e. the increase in the yield and/or production of Vitamin C which is which is directly produced from D-sorbitol or L-sorbose by increasing the activity of a SMS 37 protein. These procedures apply mutatis mutandis for other SMS proteins.

Modifications in order to have the organism produce more copies of the SMS 37 gene, i.e. overexpressing the gene, and/or protein may include the use of a strong promoter, or the mutation (e.g. insertion, deletion or point mutation) of (parts of) the SMS 37 gene or its regulatory elements. It may also involve the insertion of multiple copies of the gene into a suitable microorganism. An increase in the specific activity of an SMS 37 protein may also be accomplished by methods known in the art. Such methods may include the mutation (e.g. insertion, deletion or point mutation) of (parts of) the SMS 37 gene. A gene is said to be "overexpressed" if the level of transcription of said gene is enhanced in comparison to the wild type gene. This may be measured by for instance Northern blot analysis quantifying the amount of mRNA as an indication for gene expression. As used herein, a gene is overexpressed if the amount of generated mRNA is increased by at least 1%, 2%, 5% 10%, 25%, 50%, 75%, 100%, 200% or even more than 500%, compared to the amount of mRNA generated from a wild-type gene.

Also known in the art are methods of increasing the activity of a given protein by contacting the SMS 37 protein with specific enhancers or other substances that specifically interact with the SMS 37 protein. In order to identify such specific enhancers, the SMS 37 protein may be expressed and tested for activity in the presence of compounds suspected to enhance the activity of the SMS 37 protein. The activity of the SMS 37 protein may also be increased by stabilizing the messenger RNA encoding SMS 37. Such methods are also known in the art, see for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

The invention may be performed in/with any microorganism carrying a SMS 37 gene or equivalent or homologue thereof. Suitable microorganisms may be selected from the group consisting of yeast, algae and bacteria, either as wild type strains, mutant strains derived by classic mutagenesis and selection methods or as recombinant strains. Examples of such yeast may be, e.g., *Candida, Saccharomyces, Zygosaccharomyces, Schizosaccharomyces*, or *Kluyveromyces*. An example of such algae may be, e.g., *Chlorella*. Examples of such bacteria may be, e.g., *Gluconobacter, Acetobacter, Gluconacetobacter, Ketogulonicigenium, Pantoea, Pseudomonas*, such as, e.g., *Pseudomonas putida*, and *Escherichia*, such as, e.g., *Escherichia coli*. Preferred are *Gluconobacter* or *Acetobacter aceti*, such as for instance *G. oxydans, G. cerinus, G. frateurii, A. aceti* subsp. *xylinum* or *A. aceti* subsp. *orleanus*, preferably *G. oxydans* DSM 17078. *Gluconobacter oxydans* DSM 17078 (formerly known as *Gluconobacter oxydans* N44-1) has been deposited at Deutsche Sammlung von Mikroorganismen und Zellkulturen (DSMZ), Mascheroder Weg 1B, D-38124 Braunschweig, Germany according to the Budapest Treaty on 26. January 2005.

Microorganisms which can be used for the present invention may be publicly available from different sources, e.g., Deutsche Sammlung von Mikroorganismen und Zellkulturen (DSMZ), Mascheroder Weg 1B, D-38124 Braunschweig, Germany, American Type Culture Collection (ATCC), P.O. Box 1549, Manassas, Va. 20108 USA or Culture Collection Division, NITE Biological Resource Center, 2-5-8, Kazusakamatari, Kisarazu-shi, Chiba, 292-0818, Japan (formerly: Institute for Fermentation, Osaka (IFO), 17-85, Juso-honmachi 2-chome, Yodogawa-ku, Osaka 532-8686, Japan). Examples of preferred bacteria deposited with IFO are for instance *Gluconobacter oxydans* (formerly known as *G. melanogenus*) IFO 3293, *Gluconobacter oxydans* (formerly known as *G. melanogenus*) IFO 3292, *Gluconobacter oxydans* (formerly known as *G. rubiginosus*) IFO 3244, *Gluconobacter frateurii* (formerly known as *G. industrius*) IFO 3260, Gluconobacter cerinus IFO 3266, *Gluconobacter oxydans* IFO 3287, and *Acetobacter aceti* subsp. *orleanus* IFO 3259, which were all deposited on Apr. 5, 1954; *Acetobacter aceti* subsp. *xylinum* IFO 13693 deposited on Oct. 22, 1975, and *Acetobacter aceti* subsp. *xylinum* IFO 13773 deposited on Dec. 8, 1977. Strain *Acetobacter* sp. ATCC 15164, which is also an example of a preferred bacterium, was deposited with ATCC. Strain *Gluconobacter oxydans* (formerly known as *G. melanogenus*) N 44-1 as another example of a preferred bacterium is a derivative of the strain IFO 3293 and is described in Sugisawa et al., Agric. Biol. Chem. 54: 1201-1209, 1990.

A microorganism as of the present invention may carry further modifications either on the DNA or protein level (see above), as long as such modification has a direct impact on the yield, production and/or efficiency of the direct production of Vitamin C from substrates like e.g. D-sorbitol or L-sorbose. Such further modifications may for instance affect other genes encoding SMS proteins as described above, in particular genes encoding membrane-bound L-sorbosone dehydrogenases, such as L-sorbosone dehydrogenase SNDHai, or membrane-bound PQQ bound D-sorbitol dehydrogenases. Methods of performing such modifications are known in the art, with some examples further described herein. For the use of SNDHai for direct production of Vitamin C as well as the nucleotide and amino acid sequence thereof we refer to WO 2005/017159 which is incorporated herein by reference. Furthermore, such modification may for instance affect genes involved in the metabolization of D-sorbitol and/or L-sorbose, such as e.g. the gene or a homologue thereof as shown in SEQ ID NO:9, which acts as a repressor of SMS 37 gene, in particular a modification leading to a reduced or abolished activity of said repressor as e.g. according to SEQ ID NO:9.

The skilled person will know how to reduce or abolish the activity of said repressor, preferably a protein according to SEQ ID NO:10. Such may be for instance accomplished by either genetically modifying the host organism in such a way that it produces less or no copies of said repressor, preferably protein according to SEQ ID NO:10, than the wild type organism or by decreasing or abolishing the specific activity of said repressor, preferably the protein according to SEQ ID NO:10.

Modifications in order to have the organism produce less or no copies of such a repressor gene, preferably a gene according to SEQ ID NO:9, and/or protein according to SEQ ID NO:10 may include the use of a weak promoter, or the mutation (e.g. insertion, deletion or point mutation) of (parts of) the gene according to SEQ ID NO:9 or its regulatory elements. Decreasing or abolishing the specific activity of a protein according to SEQ ID NO:10 may also be accomplished by methods known in the art. Such methods may include the mutation (e.g. insertion, deletion or point mutation) of (parts of) a gene according to SEQ ID NO:9. This may for instance affect the interaction with DNA that is mediated by the N-terminal region of a protein according to SEQ ID NO:10 or interaction with other effector molecules.

Also known in the art are methods of reducing or abolishing the activity of a given protein by contacting the protein according to SEQ ID NO:10 with specific inhibitors or other substances that specifically interact with said protein. In order to identify such specific inhibitors, said protein may be expressed and tested for activity in the presence of compounds suspected to inhibit the activity of said protein. Potential inhibiting compounds may for instance be monoclonal or polyclonal antibodies against said protein. Such antibodies may be obtained by routine immunization protocols of suitable laboratory animals.

In accordance with a further object of the present invention there is provided the use of a polynucleotide as defined above or a microorganism which is genetically engineered using such polynucleotides in the production of Vitamin C.

The invention also relates to processes for the expression of endogenous genes in a microorganism, to processes for the production of polypeptides as defined above in a microorganism and to processes for the production of microorganisms capable of producing Vitamin C. All these processes may comprise the step of altering a microorganism, wherein "altering" as used herein encompasses the process for "genetically altering" or "altering the composition of the cell culture media and/or methods used for culturing" in such a way that the yield and/or productivity of the fermentation product can be improved compared to the wild-type organism. As used herein, "improved yield of Vitamin C" means an increase of at least 5%, 10%, 25%, 30%, 40%, 50%, 75%, 100%, 200% or even more than 500%, compared to a wild-type microorganism, i.e. a microorganism which is not genetically altered.

The term "genetically engineered" or "genetically altered" means the scientific alteration of the structure of genetic material in a living organism. It involves the production and use of recombinant DNA. More in particular it is used to delineate the genetically engineered or modified organism from the naturally occurring organism. Genetic engineering may be done by a number of techniques known in the art, such as e.g. gene replacement, gene amplification, gene disruption, transfection, transformation using plasmids, viruses, or other vectors. A genetically modified organism, e.g. genetically modified microorganism, is also often referred to as a recombinant organism, e.g. recombinant microorganism.

Thus, the present invention may include either (1) a recombinant microorganism carrying in addition to its natural gene, e.g. the gene encoding SMS 37, further copies of said gene introduced by genetic engineering of said microorganism by techniques known in the art and such as exemplified herein, or (2) a recombinant microorganism genetically engineered as above but which does not naturally carry such a gene as e.g. the gene encoding SMS 37. Preferably, a recombinant microorganism as of the present invention is modified such that it carries more copies of DNA encoding SMS 37 as the wildtype microorganism, in particular as a result of transformation with a plasmid carrying one or more copies of a DNA encoding SMS 37 or integration of such DNA encoding SMS 37 into its genome.

In accordance with still another aspect of the invention there is provided a process for the production of Vitamin C by direct fermentation.

In particular, the present invention provides a process for the direct production of Vitamin C comprising converting a substrate into Vitamin C.

Several substrates may be used as a carbon source in a process of the present invention, i.e. a process for direct conversion of a given substrate into Vitamin C such as e.g. mentioned above. Particularly suited carbon sources are those that are easily obtainable from the D-glucose or D-sorbitol metabolization pathway such as, for example, D-glucose, D-sorbitol, L-sorbose, L-sorbosone, 2-keto-L-gulonate, D-gluconate, 2-keto-D-gluconate or 2,5-diketo-gluconate. Preferably, the substrate is selected from for instance D-glucose, D-sorbitol, L-sorbose or L-sorbosone, more preferably from D-glucose, D-sorbitol or L-sorbose, and most preferably from D-sorbitol, L-sorbose or L-sorbosone. The term "substrate" and "production substrate" in connection with the above process using a microorganism is used interchangeably herein.

A medium as used herein for the above process using a microorganism may be any suitable medium for the production of Vitamin C. Typically, the medium is an aqueous medium comprising for instance salts, substrate(s), and a certain pH. The medium in which the substrate is converted into Vitamin C is also referred to as the production medium.

"Fermentation" or "production" or "fermentation process" as used herein may be the use of growing cells using media, conditions and procedures known to the skilled person, or the use of non-growing so-called resting cells, after they have been cultivated by using media, conditions and procedures known to the skilled person, under appropriate conditions for the conversion of suitable substrates into desired products such as Vitamin C. Preferably, resting cells are used for the production of Vitamin C.

The term "direct fermentation", "direct production", "direct conversion" and the like is intended to mean that a microorganism is capable of the conversion of a certain substrate into the specified product by means of one or more biological conversion steps, without the need of any additional chemical conversion step. For instance, the term "direct conversion of D-sorbitol into Vitamin C" is intended to describe a process wherein a microorganism is producing Vitamin C and wherein D-sorbitol is offered as a carbon source without the need of an intermediate chemical conversion step. A single microorganism capable of directly fermenting Vitamin C is preferred. Said microorganism is cultured under conditions which allow such conversion from the substrate as defined above.

In connection with the above process using a microorganism it is understood that the above-mentioned microorganisms also include synonyms or basonyms of such species having the same physiological properties, as defined by the International Code of Nomenclature of Prokaryotes. The nomenclature of the microorganisms as used herein is the one officially accepted (at the filing date of the priority application) by the International Committee on Systematics of Prokaryotes and the Bacteriology and Applied Microbiology Division of the International Union of Microbiological Societies, and published by its official publication vehicle International Journal of Systematic and Evolutionary Microbiology (IJSEM). A particular reference is made to Urbance et al., IJSEM (2001) vol 51:1059-1070, with a corrective notification on IJSEM (2001) vol 51:1231-1233, describing the taxonomically reclassification of *G. oxydans* DSM 4025 as *Ketogulonicigenium vulgare.*

As used herein, resting cells refer to cells of a microorganism which are for instance viable but not actively growing, or which are growing at low specific growth rates, for instance, growth rates that are lower than 0.02 $h^{-1}$, preferably lower than 0.01 $h^{-1}$. Cells which show the above growth rates are said to be in a "resting cell mode".

The process of the present invention as above using a microorganism may be performed in different steps or phases: preferably, the microorganism is cultured in a first step (also referred to as step (a) or growth phase) under conditions which enable growth. This phase is terminated by changing of the conditions such that the growth rate of the microorganism is reduced leading to resting cells, also referred to as step (b), followed by the production of Vitamin C from the substrate using the (b), also referred to as production phase.

Growth and production phase as performed in the above process using a microorganism may be performed in the same vessel, i.e., only one vessel, or in two or more different vessels, with an optional cell separation step between the two phases. The produced Vitamin C can be recovered from the cells by any suitable means. Recovering means for instance that the produced Vitamin C may be separated from the production medium. Optionally, the thus produced Vitamin C may be further processed.

For the purpose of the present invention relating to the above process using a microorganism, the terms "growth phase", "growing step", "growth step" and "growth period" are used interchangeably herein. The same applies for the terms "production phase", "production step", "production period".

One way of performing the above process using a microorganism as of the present invention may be a process wherein the microorganism is grown in a first vessel, the so-called growth vessel, as a source for the resting cells, and at least part of the cells are transferred to a second vessel, the so-called production vessel. The conditions in the production vessel may be such that the cells transferred from the growth vessel become resting cells as defined above. Vitamin C is produced in the second vessel and recovered therefrom.

In connection with the above process using a microorganism, in one aspect, the growing step can be performed in an aqueous medium, i.e. the growth medium, supplemented with appropriate nutrients for growth under aerobic conditions. The cultivation may be conducted, for instance, in batch, fed-batch, semi-continuous or continuous mode. The cultivation period may vary depending on for instance the host, pH, temperature and nutrient medium to be used, and may be for instance about 10 h to about 10 days, preferably about 1 to about 10 days, more preferably about 1 to about 5 days when run in batch or fed-batch mode, depending on the microorganism. If the cells are grown in continuous mode, the residence time may be for instance from about 2 to about 100 h, preferably from about 2 to about 50 h, depending on the microorganism. If the microorganism is selected from bacteria, the cultivation may be conducted for instance at a pH of about 3.0 to about 9.0, preferably about 4.0 to about 9.0, more preferably about 4.0 to about 8.0, even more preferably about 5.0 to about 8.0. If algae or yeast are used, the cultivation may be conducted, for instance, at a pH below about 7.0, preferably below about 6.0, more preferably below about 5.5, and most preferably below about 5.0. A suitable temperature range for carrying out the cultivation using bacteria may be for instance from about 13° C. to about 40° C., preferably from about 18° C. to about 37° C., more preferably from about 13° C. to about 36° C., and most preferably from about 18° C. to about 33° C. If algae or yeast are used, a suitable temperature range for carrying out the cultivation may be for instance from about 15° C. to about 40° C., preferably from about 20° C. to about 45° C., more preferably from about 25° C. to about 40° C., even more preferably from about 25° C. to about 38° C., and most preferably from about 30° C. to about 38° C. The culture medium for growth usually may contain such nutrients as assimilable carbon sources, e.g., glycerol, D-mannitol, D-sorbitol, L-sorbose, erythritol, ribitol, xylitol, arabitol, inositol, dulcitol, D-ribose, D-fructose, D-glucose, sucrose, and ethanol, preferably L-sorbose, D-glucose, D-sorbitol, D-mannitol, glycerol and ethanol; and digestible nitrogen sources such as organic substances, e.g., peptone, yeast extract and amino acids. The media may be with or without urea and/or corn steep liquor and/or baker's yeast. Various inorganic substances may also be used as nitrogen sources, e.g., nitrates and ammonium salts. Furthermore, the growth medium, usually may contain inorganic salts, e.g., magnesium sulfate, manganese sulfate, potassium phosphate, and calcium carbonate. Cells obtained using the procedures described above can then be further incubated at essentially the same modes, temperature and pH conditions as described above, in the presence of substrates such as D-sorbitol, L-sorbose, or D-glucose, in such a way that they convert these substrates directly into Vitamin C. Incubation can be done in a nitrogen-rich medium, containing, for example, organic nitrogen sources, e.g., peptone, yeast extract, baker's yeast, urea, amino acids, and corn steep liquor, or inorganic nitrogen sources, e.g., nitrates and ammonium salts, in which case cells will be able to further grow while producing Vitamin C. Alternatively, incubation can be done in a nitrogen-poor medium, in which case cells will not grow substantially, and will be in a resting cell mode, or biotransformation mode. In all cases, the incubation medium may also contain inorganic salts, e.g., magnesium sulfate, manganese sulfate, potassium phosphate, and calcium chloride.

In connection with the above process using a microorganism, in the growth phase the specific growth rates are for instance at least 0.02 $h^{-1}$. For cells growing in batch, fed-batch or semi-continuous mode, the growth rate depends on for instance the composition of the growth medium, pH, temperature, and the like. In general, the growth rates may be for instance in a range from about 0.05 to about 0.2 $h^{-1}$, preferably from about 0.06 to about 0.15 $h^{-1}$, and most preferably from about 0.07 to about 0.13 $h^{-1}$.

In another aspect of the above process using a microorganism, resting cells may be provided by cultivation of the respective microorganism on agar plates thus serving as growth vessel, using essentially the same conditions, e.g., cultivation period, pH, temperature, nutrient medium as described above, with the addition of agar agar.

In connection with the above process using a microorganism, if the growth and production phase are performed in two separate vessels, then the cells from the growth phase may be harvested or concentrated and transferred to a second vessel, the so-called production vessel. This vessel may contain an aqueous medium supplemented with any applicable production substrate that can be converted to Vitamin C by the cells. Cells from the growth vessel can be harvested or concentrated by any suitable operation, such as for instance centrifugation, membrane crossflow ultrafiltration or microfiltration, filtration, decantation, flocculation. The cells thus obtained may also be transferred to the production vessel in the form of the original broth from the growth vessel, without being harvested, concentrated or washed, i.e. in the form of a cell suspension. In a preferred embodiment, the cells are transferred from the growth vessel to the production vessel in the form of a cell suspension without any washing or isolating step in-between.

Thus, in a preferred embodiment of the above process using a microorganism step (a) and (c) of the process of the present invention as described above are not separated by any washing and/or separation step.

In connection with the above process using a microorganism, if the growth and production phase are performed in the same vessel, cells may be grown under appropriate conditions to the desired cell density followed by a replacement of the growth medium with the production medium containing the production substrate. Such replacement may be, for instance, the feeding of production medium to the vessel at the same time and rate as the withdrawal or harvesting of supernatant from the vessel. To keep the resting cells in the vessel, operations for cell recycling or retention may be used, such as for instance cell recycling steps. Such recycling steps, for instance, include but are not limited to methods using centrifuges, filters, membrane crossflow microfiltration of ultrafiltration steps, membrane reactors, flocculation, or cell immobilization in appropriate porous, non-porous or polymeric matrixes. After a transition phase, the vessel is brought to process conditions under which the cells are in a resting cell mode as defined above, and the production substrate is efficiently converted into Vitamin C.

The aqueous medium in the production vessel as used for the production step in connection with the above process using a microorganism, hereinafter called production medium, may contain only the production substrate(s) to be converted into Vitamin C, or may contain for instance additional inorganic salts, e.g., sodium chloride, calcium chloride, magnesium sulfate, manganese sulfate, potassium phosphate, calcium phosphate, and calcium carbonate. The production medium may also contain digestible nitrogen sources such as for instance organic substances, e.g., peptone, yeast extract, urea, amino acids, and corn steep liquor, and inorganic substances, e.g. ammonia, ammonium sulfate, and sodium nitrate, at such concentrations that the cells are kept in a resting cell mode as defined above. The medium may be with or without urea and/or corn steep liquor and/or baker's yeast. The production step may be conducted for instance in batch, fed-batch, semi-continuous or continuous mode. In case of fed-batch, semi-continuous or continuous mode, both cells from the growth vessel and production medium can be fed continuously or intermittently to the production vessel at appropriate feed rates. Alternatively, only production medium may be fed continuously or intermittently to the production vessel, while the cells coming from the growth vessel are transferred at once to the production vessel. The cells coming from the growth vessel may be used as a cell suspension within the production vessel or may be used as for instance flocculated or immobilized cells in any solid phase such as porous or polymeric matrixes. The production period, defined as the period elapsed between the entrance of the substrate into the production vessel and the harvest of the supernatant containing Vitamin C, the so-called harvest stream, can vary depending for instance on the kind and concentration of cells, pH, temperature and nutrient medium to be used, and is preferably about 2 to about 100 h. The pH and temperature can be different from the pH and temperature of the growth step, but is essentially the same as for the growth step.

In a preferred embodiment of the above process using a microorganism, the production step is conducted in continuous mode, meaning that a first feed stream containing the cells from the growth vessel and a second feed stream containing the substrate is fed continuously or intermittently to the production vessel. The first stream may either contain only the cells isolated/separated from the growth medium or a cell suspension, coming directly from the growth step, i.e. cells suspended in growth medium, without any intermediate step of cell separation, washing and/or isolating. The second feed stream as herein defined may include all other feed streams necessary for the operation of the production step, e.g. the production medium comprising the substrate in the form of one or several different streams, water for dilution, and base for pH control.

In connection with the above process using a microorganism, when both streams are fed continuously, the ratio of the feed rate of the first stream to feed rate of the second stream may vary between about 0.01 and about 10, preferably between about 0.01 and about 5, most preferably between about 0.02 and about 2. This ratio is dependent on the concentration of cells and substrate in the first and second stream, respectively.

Another way of performing the process as above using a microorganism of the present invention may be a process using a certain cell density of resting cells in the production vessel. The cell density is measured as absorbance units (optical density) at 600 nm by methods known to the skilled person. In a preferred embodiment, the cell density in the production step is at least about 10, more preferably between about 10 and about 200, even more preferably between about 15 and about 200, even more preferably between about 15 to about 120, and most preferably between about 20 and about 120.

In connection with the above process using a microorganism, in order to keep the cells in the production vessel at the desired cell density during the production phase as performed, for instance, in continuous or semi-continuous mode, any means known in the art may be used, such as for instance cell recycling by centrifugation, filtration, membrane crossflow ultrafiltration of microfiltration, decantation, flocculation, cell retention in the vessel by membrane devices or cell immobilization. Further, in case the production step is performed in continuous or semi-continuous mode and cells are continuously or intermittently fed from the growth vessel, the cell density in the production vessel may be kept at a constant level by, for instance, harvesting an amount of cells from the production vessel corresponding to the amount of cells being fed from the growth vessel.

In connection with the above process using a microorganism, the produced Vitamin C contained in the so-called harvest stream is recovered/harvested from the production vessel. The harvest stream may include, for instance, cell-free or cell-containing aqueous solution coming from the production vessel, which contains Vitamin C as a result of the conversion of production substrate by the resting cells in the production vessel. Cells still present in the harvest stream may be separated from the Vitamin C by any operations known in the art, such as for instance filtration, centrifugation, decantation, membrane crossflow ultrafiltration or microfiltration, tangential flow ultrafiltration or microfiltration or dead end filtration. After this cell separation operation, the harvest stream is essentially free of cells.

In a further aspect, the process of the present invention may be combined with further steps of separation and/or purification of the produced Vitamin C from other components contained in the harvest stream, i.e., so-called downstream processing steps. These steps may include any means known to a skilled person, such as, for instance, concentration, crystallization, precipitation, adsorption, ion exchange, electrodialysis, bipolar membrane electrodialysis and/or reverse osmosis. Vitamin C may be further purified as the free acid form or any of its known salt forms by means of operations such as for instance treatment with activated carbon, ion exchange, adsorption and elution, concentration, crystallization, filtration and drying. Specifically, a first separation of Vitamin C from other components in the harvest stream might be performed by any suitable combination or repetition of, for instance, the following methods: two- or three-compartment electrodialysis, bipolar membrane electrodialysis, reverse osmosis or adsorption on, for instance, ion exchange resins or non-ionic resins. If the resulting form of Vitamin C is a salt of L-ascorbic acid, conversion of the salt form into the free acid form may be performed by for instance bipolar membrane electrodialysis, ion exchange, simulated moving bed chromatographic techniques, and the like. Combination of the mentioned steps, e.g., electrodialysis and bipolar membrane electrodialysis into one step might be also used as well as combination of the mentioned steps e.g. several steps of ion exchange by using simulated moving bed chromatographic methods. Any of these procedures alone or in combination constitute a convenient means for isolating and purifying the product, i.e. Vitamin C. The product thus obtained may further be isolated in a manner such as, e.g. by concentration, crystallization, precipitation, washing and drying of the crystals and/or further purified by, for instance, treatment with activated carbon, ion exchange and/or re-crystallization.

In a preferred embodiment, Vitamin C is purified from the harvest stream by a series of downstream processing steps as described above without having to be transferred to a non-aqueous solution at any time of this processing, i.e. all steps are performed in an aqueous environment. Such preferred downstream processing procedure may include for instance the concentration of the harvest stream coming from the production vessel by means of two- or three-compartment electrodialysis, conversion of Vitamin C in its salt form present in the concentrated solution into its acid form by means of bipolar membrane electrodialysis and/or ion exchange, purification by methods such as for instance treatment with activated carbon, ion exchange or non-ionic resins, followed by a further concentration step and crystallization. These crystals can be separated, washed and dried. If necessary, the crystals may be again re-solubilized in water, treated with activated carbon and/or ion exchange resins and recrystallized. These crystals can then be separated, washed and dried.

Advantageous embodiments of the invention become evident from the dependent claims. These and other aspects and embodiments of the present invention should be apparent to those skilled in the art from the teachings herein.

The sequence of the gene comprising a nucleotide sequence according to SEQ ID NO:1 encoding a SMS 37 protein was determined by sequencing a genomic clone obtained from *Gluconobacter oxydans* DSM 17078.

The invention also relates to a polynucleotide encoding at least a biologically active fragment or derivative of a SMS 37 polypeptide as shown in SEQ ID NO:2.

As used herein, "biologically active fragment or derivative" means a polypeptide which retains essentially the same biological function or activity as the polypeptide shown in SEQ ID NO:2. Examples of biological activity may for instance be enzymatic activity, signaling activity or antibody reactivity. The term "same biological function" or "functional equivalent" as used herein means that the protein has essentially the same biological activity, e.g. enzymatic, signaling or antibody reactivity, as a polypeptide shown in SEQ ID NO:2.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living microorganism is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment.

An isolated polynucleotide or nucleic acid as used herein may be a DNA or RNA that is not immediately contiguous with both of the coding sequences with which it is immediately contiguous (one on the 5'-end and one on the 3'-end) in the naturally occurring genome of the organism from which it is derived. Thus, in one embodiment, a nucleic acid includes some or all of the 5'-non-coding (e.g., promoter) sequences that are immediately contiguous to the coding sequence. The term "isolated polynucleotide" therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an “isolated nucleic acid fragment” is a nucleic acid fragment that is not naturally occurring as a fragment and would not be found in the natural state.

As used herein, the terms “polynucleotide”, “gene” and “recombinant gene” refer to nucleic acid molecules which may be isolated from chromosomal DNA, which include an open reading frame encoding a protein, e.g. *G. oxydans* DSM 17078 STS proteins. A polynucleotide may include a polynucleotide sequence as shown in SEQ ID NO:1 or fragments thereof and regions upstream and downstream of the gene sequences which may include, for example, promoter regions, regulator regions and terminator regions important for the appropriate expression and stabilization of the polypeptide derived thereof.

A gene may include coding sequences, non-coding sequences such as for instance untranslated sequences located at the 3'- and 5'-ends of the coding region of a gene, and regulatory sequences. Moreover, a gene refers to an isolated nucleic acid molecule as defined herein. It is furthermore appreciated by the skilled person that DNA sequence polymorphisms that lead to changes in the amino acid sequences of SMS proteins may exist within a population, e.g., the *Gluconobacter oxydans* population. Such genetic polymorphism in the SMS 37 gene may exist among individuals within a population due to natural variation or in cells from different populations. Such natural variations can typically result in 1-5% variance in the nucleotide sequence of the SMS 37 gene. Any and all such nucleotide variations and the resulting amino acid polymorphism in SMS 37 are the result of natural variation and that do not alter the functional activity of SMS proteins are intended to be within the scope of the invention.

As used herein, the terms “polynucleotide” or “nucleic acid molecule” are intended to include DNA molecules (e.g., cDNA or genomic DNA) and RNA molecules (e.g., mRNA) and analogs of the DNA or RNA generated using nucleotide analogs. The nucleic acid molecule may be single-stranded or double-stranded, but preferably is double-stranded DNA. The nucleic acid may be synthesized using oligonucleotide analogs or derivatives (e.g., inosine or phosphorothioate nucleotides). Such oligonucleotides may be used, for example, to prepare nucleic acids that have altered base-pairing abilities or increased resistance to nucleases.

The sequence information as provided herein should not be so narrowly construed as to require inclusion of erroneously identified bases. The specific sequences disclosed herein may be readily used to isolate the complete gene from a recombinant or non-recombinant microorganism capable of converting a given carbon source directly into Vitamin C, in particular *Gluconobacter oxydans*, preferably *Gluconobacter oxydans* DSM 17078 which in turn may easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence may be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

A nucleic acid molecule according to the invention may comprise only a portion or a fragment of the nucleic acid sequence provided by the present invention, such as for instance the sequence shown in SEQ ID NO:1, for example a fragment which may be used as a probe or primer such as for instance SEQ ID NO:3 or SEQ ID NO:4 or a fragment encoding a portion of a protein according to the invention. The nucleotide sequence determined from the cloning of the SMS 37 gene allows for the generation of probes and primers designed for use in identifying and/or cloning other SMS 37 family members, as well as SMS 37 homologues from other species. The probe/primer typically comprises substantially purified oligonucleotides which typically comprises a region of nucleotide sequence that hybridizes preferably under highly stringent conditions to at least about 12 or 15, preferably about 18 or 20, more preferably about 22 or 25, even more preferably about 30, 35, 40, 45, 50, 55, 60, 65, or 75 or more consecutive nucleotides of a nucleotide sequence shown in SEQ ID NO:1 or a fragment or derivative thereof.

A nucleic acid molecule encompassing all or a portion of the nucleic acid sequence of SEQ ID NO:1 may be also isolated by the polymerase chain reaction (PCR) using synthetic oligonucleotide primers designed based upon the sequence information contained herein.

A nucleic acid of the invention may be amplified using cDNA, mRNA or alternatively, genomic DNA, as a template and appropriate oligonucleotide primers according to standard PCR amplification techniques. The nucleic acid thus amplified may be cloned into an appropriate vector and characterized by DNA sequence analysis.

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides, may be used as hybridization probes or polymerase chain reaction (PCR) primers. Uses of the nucleic acid molecules of the present invention that do not encode a polypeptide having a SMS 37 activity include, inter alia, (1) isolating the gene encoding the protein of the present invention, or allelic variants thereof from a cDNA library, e.g., from other organisms than *Gluconobacter oxydans* and (2) Northern blot analysis for detecting expression of mRNA of said protein in specific cells or (3) use in enhancing and/or improving the function or activity of homologous SMS 37 genes in said other organisms.

Probes based on the nucleotide sequences provided herein may be used to detect transcripts or genomic sequences encoding the same or homologous proteins for instance in other organisms. Nucleic acid molecules corresponding to natural variants and non-*G. oxydans* homologues of the *G. oxydans* SMS 37 DNA of the invention which are also embraced by the present invention may be isolated based on their homology to the *G. oxydans* SMS 37 nucleic acid disclosed herein using the *G. oxydans* DNA, or a portion thereof, as a hybridization probe according to standard hybridization techniques, preferably under highly stringent hybridization conditions.

In preferred embodiments, the probe further comprises a label group attached thereto, e.g., the label group can be a radioisotope, a fluorescent compound, an enzyme, or an enzyme cofactor.

Homologous gene sequences may be isolated, for example, by performing PCR using two degenerate oligonucleotide primer pools designed on the basis of nucleotide sequences as taught herein.

The template for the reaction may be cDNA obtained by reverse transcription of mRNA prepared from strains known or suspected to express a polynucleotide according to the invention. The PCR product may be subcloned and sequenced to ensure that the amplified sequences represent the sequences of a new nucleic acid sequence as described herein, or a functional equivalent thereof.

The PCR fragment may then be used to isolate a full length cDNA clone by a variety of known methods. For example, the amplified fragment may be labeled and used to screen a bacteriophage or cosmid cDNA library. Alternatively, the labeled fragment may be used to screen a genomic library.

PCR technology can also be used to isolate full-length cDNA sequences from other organisms. For example, RNA may be isolated, following standard procedures, from an appropriate cellular or tissue source. A reverse transcription reaction may be performed on the RNA using an oligonucleotide primer specific for the most 5'-end of the amplified fragment for the priming of first strand synthesis.

The resulting RNA/DNA hybrid may then be "tailed" (e.g., with guanines) using a standard terminal transferase reaction, the hybrid may be digested with RNaseH, and second strand synthesis may then be primed (e.g., with a poly-C primer). Thus, cDNA sequences upstream of the amplified fragment may easily be isolated. For a review of useful cloning strategies, see e.g., Sambrook et al., supra; and Ausubel et al., supra.

Also, nucleic acids encoding other SMS 37 family members, which thus have a nucleotide sequence that differs from a nucleotide sequence according to SEQ ID NO:1, are within the scope of the invention. Moreover, nucleic acids encoding SMS 37 proteins from different species which thus may have a nucleotide sequence which differs from a nucleotide sequence shown in SEQ ID NO:1 are within the scope of the invention.

The invention also relates to an isolated polynucleotide hybridisable under stringent conditions, preferably under highly stringent conditions, to a polynucleotide as of the present invention, such as for instance a polynucleotide shown in SEQ ID NO:1. Advantageously, such polynucleotide may be obtained from a microorganism capable of converting a given carbon source directly into Vitamin C, in particular *Gluconobacter oxydans*, preferably *Gluconobacter oxydans* DSM 17078.

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, most preferably at least 95% homologous to each other typically remain hybridized to each other.

In one embodiment, a nucleic acid of the invention is at least 40%, 45%, 50%, 55%, 60%, 65%, 70%, 75%, 80%, 85%, 90%, 91%, 92%, 93%, 94%, 95%, 96%, 97%, 98%, 99%, or more homologous to a nucleic acid sequence shown in SEQ ID NO:1 or the complement thereof.

A preferred, non-limiting example of stringent hybridization conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C.

Highly stringent conditions include incubations at 42° C. for a period of several days, such as 2-4 days, using a labeled DNA probe, such as a digoxigenin (DIG)-labeled DNA probe, followed by one or more washes in 2×SSC, 0.1% SDS at room temperature and one or more washes in 0.5×SSC, 0.1% SDS or 0.1×SSC, 0.1% SDS at 65-68° C. In particular, highly stringent conditions include, for example, 2 h to 4 days incubation at 42° C. using a DIG-labeled DNA probe (prepared by e.g. using a DIG labeling system; Roche Diagnostics GmbH, 68298 Mannheim, Germany) in a solution such as DigEasyHyb solution (Roche Diagnostics GmbH) with or without 100 μg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

Preferably, an isolated nucleic acid molecule of the invention that hybridizes under preferably highly stringent conditions to a nucleotide sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *G. oxydans* SMS 37 protein.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.). Of course, a polynucleotide which hybridizes only to a poly (A) sequence (such as the 3'-terminal poly (A) tract of mRNAs), or to a complementary stretch of T (or U) residues, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

In a typical approach, genomic DNA or cDNA libraries constructed from other organisms, e.g. microorganisms capable of converting a given carbon source directly into Vitamin C, in particular other Gluconobacter species may be screened.

For example, Gluconobacter strains may be screened for homologous polynucleotides by Southern and/or Northern blot analysis. Upon detection of transcripts homologous to polynucleotides according to the invention, DNA libraries may be constructed from RNA isolated from the appropriate strain, utilizing standard techniques well known to those of skill in the art. Alternatively, a total genomic DNA library may be screened using a probe hybridisable to a polynucleotide according to the invention.

A nucleic acid molecule of the present invention, such as for instance a nucleic acid molecule shown in SEQ ID NO:1 or a fragment or derivative thereof, may be isolated using standard molecular biology techniques and the sequence information provided herein. For example, using all or portion of the nucleic acid sequence shown in SEQ ID NO:1 as a hybridization probe, nucleic acid molecules according to the invention may be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Furthermore, oligonucleotides corresponding to or hybridisable to nucleotide sequences according to the invention may be prepared by standard synthetic techniques, e.g., using an automated DNA synthesizer.

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions)×100). Preferably, the two sequences are the same length.

The skilled person will be aware of the fact that several different computer programs are available to determine the homology between two sequences. For instance, a comparison of sequences and determination of percent identity between two sequences may be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at URL accelrys[dot]com), using either a Blossom 62 matrix or a PAM250 matrix, and a gap weight of 16, 14, 12, 10, 8, 6 or 4 and a length weight of 1, 2, 3, 4, 5 or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available at URL accelrys[dot]com), using a NWSgapdna.CMP matrix and a gap weight of 40, 50, 60, 70 or 80 and a length weight of 1, 2, 3, 4, 5 or 6. In another embodiment, the percent identity between two amino acid or nucleotide sequences is determined using the algorithm of E. Meyers and W. Miller (CABIOS, 4:11-17 (1989) which has been incorporated into the ALIGN program (version 2.0) (available at URL vega[dot]igh[dot]cnrs[dot]fr[slash]bin[slash]aliqn-guess[dot]cgi) using a PAM120 weight residue table, a gap length penalty of 12 and a gap penalty of 4.

The nucleic acid and protein sequences of the present invention may further be used as a "query sequence" to perform a search against public databases to, for example, identify other family members or related sequences. Such searches may be performed using the BLASTN and BLASTX programs (version 2.0) of Altschul, et al. (1990) J. Mol. Biol. 215:403-10. BLAST nucleotide searches may be performed with the BLASTN program, score =100, word length =12 to obtain nucleotide sequences homologous to the nucleic acid molecules of the present invention. BLAST protein searches may be performed with the BLASTX program, score =50, word length =3 to obtain amino acid sequences homologous to the protein molecules of the present invention. To obtain gapped alignments for comparison purposes, Gapped BLAST may be utilized as described in Altschul et al., (1997) Nucleic Acids Res. 25 (17): 3389-3402.

When utilizing BLAST and Gapped BLAST programs, the default parameters of the respective programs (e.g., BLASTX and BLASTN) may be used. See URL ncb[dot]nlm[dot]nih[dot]gov.

In another preferred embodiment, an isolated nucleic acid molecule of the invention comprises a nucleic acid molecule which is the complement of a nucleotide sequence as of the present invention, such as for instance the sequence shown in SEQ ID NO:1. A nucleic acid molecule, which is complementary to a nucleotide sequence disclosed herein, is one that is sufficiently complementary to a nucleotide sequence shown in SEQ ID NO:1 such that it may hybridize to said nucleotide sequence thereby forming a stable duplex.

In a further preferred embodiment, a nucleic acid of the invention as shown in SEQ ID NO:1 or the complement thereof contains at least one mutation leading to a gene product with modified function/activity. The at least one mutation may be introduced by methods described herein. In one aspect, the at least one mutation leads to a SMS 37 protein whose function and/or activity compared to the wild type counterpart is enhanced or improved. Methods for introducing such mutations are well known in the art.

The term "increase" of activity as used herein encompasses increasing activity of one or more polypeptides in the producing organism, which in turn are encoded by the corresponding polynucleotides described herein. There are a number of methods available in the art to accomplish increase of activity of a given protein, in this case the SMS 37 protein. In general, the specific activity of a protein may be increased or the copy number of the protein may be increased. The term increase of activity or equivalent expressions also encompasses the situation wherein SMS 37 protein activity is introduced in a cell that did not contain this activity before, e.g. by introducing a gene encoding SMS 37 in a cell that did not contain an equivalent of this gene before, or that could not express an active form of the corresponding protein before.

To facilitate such an increase, the copy number of the genes corresponding to the polynucleotides described herein may be increased. Alternatively, a strong promoter may be used to direct the expression of the polynucleotide. In another embodiment, the promoter, regulatory region and/or the ribosome binding site upstream of the gene can be altered to increase the expression. The expression may also be enhanced or increased by increasing the relative half-life of the messenger RNA. In another embodiment, the activity of the polypeptide itself may be increased by employing one or more mutations in the polypeptide amino acid sequence, which increase the activity. For example, altering the affinity of the polypeptide for its corresponding substrate may result in improved activity. Likewise, the relative half-life of the polypeptide may be increased. In either scenario, that being enhanced gene expression or increased specific activity, the improvement may be achieved by altering the composition of the cell culture media and/or methods used for culturing. “Enhanced expression” or “improved activity” as used herein means an increase of at least 5%, 10%, 25%, 50%, 75%, 100%, 200% or even more than 500%, compared to a wild-type protein, polynucleotide, gene; or the activity and/or the concentration of the protein present before the polynucleotides or polypeptides are enhanced and/or improved. The activity of the SMS 37 protein may also be enhanced by contacting the protein with a specific or general enhancer of its activity.

Another aspect of the invention pertains to vectors, containing a nucleic acid encoding a protein according to the invention or a functional equivalent or portion thereof. As used herein, the term “vector” refers to a nucleic acid molecule capable of transporting another nucleic acid to which it has been linked. One type of vector is a “plasmid”, which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome.

Moreover, certain vectors are capable of directing the expression of genes to which they are operatively linked. Such vectors are referred to herein as “expression vectors”. In general, expression vectors of utility in recombinant DNA techniques are often in the form of plasmids. The terms “plasmid” and “vector” can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, “operatively linked” is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term “regulatory sequence” is intended to include promoters, enhancers and other expression control elements (e.g., attenuator). Such regulatory sequences are described, for example, in Goeddel; Gene Expression Technology: Methods in Enzymology 185, Academic Press, San Diego, Calif. (1990). Regulatory sequences include those which direct constitutive or inducible expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention may be introduced into host cells to thereby produce proteins or peptides, encoded by nucleic acids as described herein, including, but not limited to, mutant proteins, fragments thereof, variants or functional equivalents thereof, and fusion proteins, encoded by a nucleic acid as described herein, e.g., SMS 37 proteins, mutant forms of SMS 37 proteins, fusion proteins and the like.

The recombinant expression vectors of the invention may be designed for expression of SMS 37 proteins in a suitable microorganism. For example, a protein according to the invention may be expressed in bacterial cells such as strains belonging to the genera *Gluconobacter, Gluconacetobacter* or *Acetobacter*. Expression vectors useful in the present invention include chromosomal-, episomal- and virus-derived vectors e.g., vectors derived from bacterial plasmids, bacteriophage, and vectors derived from combinations thereof, such as those derived from plasmid and bacteriophage genetic elements, such as cosmids and phagemids.

The DNA insert may be operatively linked to an appropriate promoter, which may be either a constitutive or inducible promoter. The skilled person will know how to select suitable promoters. The expression constructs may contain sites for transcription initiation, termination, and, in the transcribed region, a ribosome binding site for translation. The coding portion of the mature transcripts expressed by the constructs may preferably include an initiation codon at the beginning and a termination codon appropriately positioned at the end of the polypeptide to be translated.

Vector DNA may be introduced into suitable host cells via conventional transformation or transfection techniques. As used herein, the terms “transformation”, “transconjugation” and “transfection” are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipidmediated transfection or electroporation. Suitable methods for transforming or transfecting host cells may be found in Sambrook, et al. (supra), Davis et al., Basic Methods in Molecular Biology (1986) and other laboratory manuals.

In order to identify and select cells which have integrated the foreign DNA into their genome, a gene that encodes a selectable marker (e.g., resistance to antibiotics) is generally introduced into the host cells along with the gene of interest. Preferred selectable markers include those that confer resistance to drugs, such as kanamycin, tetracycline, ampicillin and streptomycin. A nucleic acid encoding a selectable marker is preferably introduced into a host cell on the same vector as that encoding a protein according to the invention or can be introduced on a separate vector such as, for example, a suicide vector, which cannot replicate in the host cells. Cells stably transfected with the introduced nucleic acid can be identified by drug selection (e.g., cells that have incorporated the selectable marker gene will survive, while the other cells die).

The invention provides also an isolated polypeptide having the amino acid sequence shown in SEQ ID NO:2 or an amino acid sequence obtainable by expressing a polynucleotide of the present invention, such as for instance a polynucleotide sequence shown in SEQ ID NO:1 in an appropriate host.

Polypeptides according to the invention may contain only conservative substitutions of one or more amino acids in the amino acid sequence represented by SEQ ID NO:2 or substitutions, insertions or deletions of non-essential amino acids. Accordingly, a non-essential amino acid is a residue that may be altered in the amino acid sequences shown in SEQ ID NO:2 without substantially altering the biological function.

For example, amino acid residues that are conserved among the proteins of the present invention, are predicted to be particularly unamenable to alteration. Furthermore, amino acids conserved among the proteins according to the present invention and other SMS 37 proteins are not likely to be amenable to alteration.

The term "conservative substitution" is intended to mean that a substitution in which the amino acid residue is replaced with an amino acid residue having a similar side chain. These families are known in the art and include amino acids with basic side chains (e.g., lysine, arginine and histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). As mentioned above, the polynucleotides of the invention may be utilized in the genetic engineering of a suitable host cell to make it better and more efficient in the fermentation, for example in a direct fermentation process for Vitamin C.

According to the invention a genetically engineered/recombinantly produced host cell (also referred to as recombinant cell or transformed cell) carrying such a modified polynucleotide wherein the function of the linked protein is significantly modified in comparison to a wild-type cell such that the yield, production and/or efficiency of production of one or more fermentation products such as Vitamin C is improved. The host cell may be selected from a microorganism capable of directly producing one or more fermentation products such as for instance Vitamin C from a given carbon source, in particular *Gluconobacter oxydans*, preferably *G. oxydans* DSM 17078.

A "transformed cell" or "recombinant cell" is a cell into which (or into an ancestor of which) has been introduced, by means of recombinant DNA techniques, a nucleic acid according to the invention, or wherein the activity of the SMS 37 protein has been increased and/or enhanced. Suitable host cells include cells of microorganisms capable of producing a given fermentation product, e.g., converting a given carbon source directly into Vitamin C. In particular, these include strains from the genera *Pseudomonas, Pantoea, Escherichia, Corynebacterium, Ketogulonicigenium* and acetic acid bacteria like e.g., *Gluconobacter, Acetobacter* or *Gluconacetobacter*, preferably *Acetobacter* sp., *Acetobacter aceti, Gluconobacter frateurii, Gluconobacter cerinus, Gluconobacter thailandicus, Gluconobacter oxydans*, more preferably *G. oxydans*, most preferably *G. oxydans* DSM 17078.

Improved gene expression may also be achieved by modifying the SMS 37 gene, e.g., by introducing one or more mutations into the SMS 37 gene wherein said modification leads to a SMS 37 protein with a function which is significantly improved in comparison to the wild-type protein.

Therefore, in one other embodiment, the polynucleotide carrying the at least one mutation is derived from a polynucleotide as represented by SEQ ID NO:1 or equivalents thereof.

A mutation as used herein may be any mutation leading to a more functional or more stable polypeptide, e.g. more functional or more stable SMS 37 gene products. This may include for instance an alteration in the genome of a microorganism, which improves the synthesis of SMS 37 or leads to the expression of a SMS 37 protein with an altered amino acid sequence whose function compared with the wild type counterpart having a non-altered amino acid sequence is improved and/or enhanced. The improvement may occur at the transcriptional, translational or post-translational level.

The alteration in the genome of the microorganism may be obtained e.g. by replacing through a single or double crossover recombination a wild type DNA sequence by a DNA sequence containing the alteration. For convenient selection of transformants of the microorganism with the alteration in its genome the alteration may, e.g. be a DNA sequence encoding an antibiotic resistance marker or a gene complementing a possible auxotrophy of the microorganism. Mutations include, but are not limited to, deletion-insertion mutations.

An alteration in the genome of the microorganism leading to a more functional polypeptide may also be obtained by randomly mutagenizing the genome of the microorganism using e.g. chemical mutagens, radiation or transposons and selecting or screening for mutants which are better or more efficient producers of one or more fermentation products. Standard methods for screening and selection are known to the skilled person.

In a specific embodiment, it is desired to knockout or suppress a repressor of the SMS 37 gene of the present invention, i.e., wherein its repressor gene expression is artificially suppressed in order to improve the yield, productivity, and/or efficiency of production of the fermentation product when introduced into a suitable host cell. Methods of providing knockouts as well as microorganisms carrying such suppressed genes are well known in the art. The suppression of the repressor gene may be induced by deleting at least a part of the repressor gene or the regulatory region thereof. As used herein, "suppression of the gene expression" includes complete and partial suppression, as well as suppression under specific conditions and also suppression of the expression of either one of the two alleles.

The aforementioned mutagenesis strategies for SMS 37 proteins may result in increased yields of a desired compound in particular Vitamin C. This list is not meant to be limiting; variations on these mutagenesis strategies will be readily apparent to one of ordinary skill in the art. By these mechanisms, the nucleic acid and protein molecules of the invention may be utilized to generate microorganisms such as *Gluconobacter oxydans* or related strains of bacteria expressing mutated SMS 37 nucleic acid and protein molecules such that the yield, productivity, and/or efficiency of production of a desired compound such as Vitamin C is improved.

In connection with the above process using a microorganism, in one aspect, the process of the present invention leads to yields of Vitamin C which are in general at least about more than 5.7 g/l, such as 10 g/l, 20 g/l, 50 g/l, 100 g/l, 200 g/l, 300 g/l, 400 g/l or more than 600 g/l. In one embodiment, the yield of Vitamin C produced by the process of the present invention is in the range of from about more than 5.7 to about 600 g/l. The yield of Vitamin C refers to the concentration of Vitamin C in the harvest stream coming directly out of the production vessel, i.e. the cell-free supernatant comprising the Vitamin C.

In one aspect of the invention, microorganisms (in particular from the genera of *Gluconobacter, Gluconacetobacter* and *Acetobacter*) are provided that are able to directly produce Vitamin C from a suitable carbon source like D-sorbitol and/or L-sorbose. When measured for instance in a resting cell method after an incubation period of 20 hours, these organisms were found to be able to produce Vitamin C directly from D-sorbitol or L-sorbose, even up to a level of 280 mg/l and 670 mg/l respectively. In another aspect of the invention, a microorganism is provided capable of directly producing Vitamin C in quantities of 300 mg/l when starting from D-sorbitol or more or 800 mg/l or more when starting from L-sorbose, respectively when for instance measured in a resting cell method after an incubation period of 20 hours.

Such may be achieved by increasing the activity of a STS polypeptide, preferably a SMS 37 polypeptide. The yield of Vitamin C produced from D-sorbitol may even be as high as 400, 600, 1000 mg/l or even exceed 1.5, 2, 4, 10, 20, 50 g/l. The yield of Vitamin C produced from L-sorbose may even be as high as 1000 mg/l or even exceed 1.5, 2, 4, 10, 20, 50 g/l. Preferably, these amounts of Vitamin C can be achieved when measured by resting cell method after an incubation period of 20 hours.

As used herein, measurement in a "resting cell method" comprises (i) growing the cells by means of any method well know to the person skilled in the art, (ii) harvesting the cells from the growth broth, and (iii) incubating the harvested cells in a medium containing the substrate which is to be converted into the desired product, e.g. Vitamin C, under conditions where the cells do not grow any longer, i.e. there is no increase in the amount of biomass during this so-called conversion step.

The recombinant microorganism carrying e.g. a modified SMS 37 gene and which is able to produce the fermentation product in significantly higher yield, productivity, and/or efficiency may be cultured in an aqueous medium supplemented with appropriate nutrients under aerobic conditions as described above.

The nucleic acid molecules, polypeptides, vectors, primers, and recombinant microorganisms described herein may be used in one or more of the following methods: identification of *Gluconobacter oxydans* and related organisms; mapping of genomes of organisms related to *Gluconobacter oxydans*; identification and localization of *Gluconobacter oxydans* sequences of interest; evolutionary studies; determination of SMS 37 protein regions required for function; modulation of a SMS 37 protein activity or function; modulation of the activity of a SMS pathway; and modulation of cellular production of a desired compound, such as Vitamin C.

The invention provides methods for screening molecules which modulate the activity of a SMS 37 protein, either by interacting with the protein itself or a substrate or binding partner of the SMS 37 protein, or by modulating the transcription or translation of a SMS 37 nucleic acid molecule of the invention. In such methods, a microorganism expressing one or more SMS 37 proteins of the invention is contacted with one or more test compounds, and the effect of each test compound on the activity or level of expression of the SMS 37 protein is assessed.

The biological, enzymatic or other activity of SMS proteins can be measured by methods well known to a skilled person, such as, for example, by incubating a cell fraction in containing the SMS protein in the presence of its substrate, electron acceptor(s) or donor(s) including phenazine methosulfate (PMS), dichlorophenol-indophenol (DCIP), NAD, NADH, NADP, NADPH, which consumption can be directly or indirectly measured by photometric, colorimetric or fluorimetric methods, and other inorganic components which might be relevant for the development of the activity. Thus, for example, the activity of membrane-bound D-sorbitol dehydrogenase can be measured in an assay where membrane fractions containing this enzyme are incubated in the presence of phosphate buffer at pH 6, D-sorbitol and the artificial electron acceptors DCIP and PMS. The rate of consumption of DCIP can be measured at 600 nm, and is directly proportional to the D-sorbitol dehydrogenase activity present in the membrane fraction.

In case of transporters, such as e.g. importer, symporters or exporters, the activity of such SMS proteins can be measured by methods well known to a skilled person, such as, for example, by incubating a membrane fraction containing the SMS protein with the radioactively marked sugar or sugar alcohol which can be actively transported by the SMS protein. The activity of the transporter is directly proportional to (1) the amount of radioactivity incorporated into the cell mass, if the SMS protein is involved in import of sugar or sugar alcohols into the cytoplasm or (2) the amount of radioactivity accumulated outside the cytoplasm into the periplasm/extracellular environment, if the SMS protein is involved in export of sugar or sugar alcohols, such as e.g. sorbosone, outside the cytoplasm. Thus, for example, the activity of a transporter can be measured in an assay where intact cells containing the specific transporter are incubated in the presence of phosphate buffer at pH 6 and the radioactively marked carbon source such as e.g. glucose, galactose or sorbosone. The rate of assimilation of radioactive carbon source such as e.g. glucose, galactose or sorbosone by the cells can be measured by methods known to the skilled person, and is directly proportional to the SMS protein activity present in the membrane fraction, if the transport from outside into the cytoplasm should be measured. In the case of exporters, one can also generate inverted membranes, e.g. inside-out vesicles and measure the uptake of radioactivity as described above.

A further method of measuring the activity of exporters such as, e.g. SMS 37, may be via determination of the extracellular level of compounds produced in the cytoplasm, such as e.g. sorbosone, but which require export to the periplasm or extracellular environment performed by said exporter and comparing this level to a situation wherein efflux system is not present, such as e.g. knockout mutants wherein the gene encoding said exporter is not active any more, and thus extracellular levels may decrease. In contrast, overexpression of such a gene encoding said exporter may result in increased extracellular levels of the compound such as, e.g. sorbosone.

It may be evident from the above description that the fermentation product of the methods according to the invention may not be limited to Vitamin C alone. The "desired compound" or "fermentation product" as used herein may be any natural product of *Gluconobacter oxydans*, which includes the final products and intermediates of biosynthesis pathways, such as for example L-sorbose, L-sorbosone, D-gluconate, 2-keto-D-gluconate, 5-keto-D-gluconate, 2,5-diketo-D-gluconate and 2-keto-L-gulonate (2-KGA), in particular the biosynthetic generation of Vitamin C.

Thus, the present invention is directed to the use of a polynucleotide, polypeptide, vector, primer and recombinant microorganism as described herein in the production of Vitamin C, i.e., the direct conversion of a carbon source into Vitamin C. In a preferred embodiment, a modified polynucleotide, polypeptide, vector and recombinant microorganism as described herein is used for improving the yield, productivity, and/or efficiency of the production of Vitamin C.

The terms "production" or "productivity" are art-recognized and include the concentration of the fermentation product (for example, Vitamin C) formed within a given time and a given fermentation volume (e.g., kg product per hour per liter). The term "efficiency of production" includes the time required for a particular level of production to be achieved (for example, how long it takes for the cell to attain a particular rate of output of a fermentation product). The term "yield" is art-recognized and includes the efficiency of the conversion of the carbon source into the product e., Vitamin C). This is generally written as, for example, kg product per kg carbon source. By "increasing the yield and/or production/productivity" of the compound it is meant that the quantity of recovered molecules, or of useful recovered molecules of that compound in a given amount of culture over a given amount of time is increased. The terms "biosynthesis" or a "biosynthetic pathway" are art-recognized and include the synthesis of a compound, preferably an organic compound, by a cell from intermediate compounds in what may be a multistep and highly regulated process. The language "metabolism" is art-recognized and includes the totality of the biochemical reactions that take place in an organism. The metabolism of a particular compound, then, (e.g., the metabolism of an amino acid such as glycine) comprises the overall biosynthetic, modification, and degradation pathways in the cell related to this compound. The language "transport" or "import" is art-recognized and includes the facilitated movement of one or more molecules across a cellular membrane through which the molecule would otherwise either be unable to pass or be passed inefficiently.

Vitamin C as used herein may be any chemical form of L-ascorbic acid found in aqueous solutions, such as for instance undissociated, in its free acid form or dissociated as an anion. The solubilized salt form of L-ascorbic acid may be characterized as the anion in the presence of any kind of cations usually found in fermentation supernatants, such as for instance potassium, sodium, ammonium, or calcium. Also included may be isolated crystals of the free acid form of L-ascorbic acid. On the other hand, isolated crystals of a salt form of L-ascorbic acid are called by their corresponding salt name, i.e. sodium ascorbate, potassium ascorbate, calcium ascorbate and the like.

In one preferred embodiment, the present invention is related to a process for the production of Vitamin C wherein a nucleotide according to the invention or a modified polynucleotide sequence as described above is introduced into a suitable microorganism, the recombinant microorganism is cultured under conditions that allow the production of Vitamin C in high productivity, yield, and/or efficiency, the produced fermentation product is isolated from the culture medium and optionally further purified. Suitable host microorganisms may be selected from e.g. *G. oxydans* DSM 17078, *G. oxydans* IFO 3293, *G. oxydans* IFO 3292, *G. oxydans* ATCC 621H, *G. oxydans* IFO 12528, *G. oxydans* T-100 *G. oxydans* IFO 3291, *G. oxydans* IFO 3255, *G. oxydans* ATCC 9937, *G. oxydans* ATCC 9937, *G. oxydans* IFO 3244, *G. cerinus* IFO 3266, *G. frateurii* IFO 3260, *G. oxydans* IFO 3287, *G. thailandicus* NBRC 100600 or *Gluconoacetobacter liquefaciens* ATCC 14835.

This invention is further illustrated by the following examples which should not be construed as limiting. The contents of all references, patent applications, patents and published patent applications, cited throughout this application are hereby incorporated by reference.

EXAMPLES

Example 1

Preparation of Chromosomal DNA and Amplification of DNA Fragment by PCR

Chromosomal DNA of *Gluconobacter oxydans* DSM 17078 was prepared from the cells cultivated at 30° C. for 1 day in mannitol broth (MB) liquid medium consisting of 25 g/l mannitol, 5 g/l of yeast extract (Difco), and 3 g/l of Bactopeptone (Difco) by the method described by Sambrook et al (1989) "Molecular Cloning: A Laboratory Manual/Second Edition", Cold Spring Harbor Laboratory Press).

A DNA fragment was prepared by PCR with the chromosomal DNA prepared above and a set of primers, Pf (SEQ ID NO:3) and Pr (SEQ ID NO:4). For the reaction, the Expand High Fidelity PCR kit (Roche Diagnostics) and 10 ng of the chromosomal DNA was used in total volume of 100 μl according to the supplier's instruction to have the PCR product containing SMS 37 DNA sequence (SEQ ID NO:1). The PCR product was recovered from the reaction and its correct sequence confirmed.

Example 2

Overexpression of the SMS 37 Gene in *G. oxydans* DSM 17078

To upregulate the expression of the SMS 37 gene, an overexpression system using a plasmid construct was used. Herein, the SMS 37 gene was fused to a strong constitutive promoter, and the construct was then introduced into *G. oxydans* DSM 17078. The overexpression of the SMS 37 gene is determined through standard methods known to those skilled in the art, such as transcript analysis using Northern Blot, RT-PCR or other technology, protein expression determination using Western Blot, two-dimensional gel electrophoresis, protein activity determination using specific enzyme assays or through direct measurement of product formation or substrate conversion.

The promoter can be any promoter that exhibits strong constitutive activity in *Gluconobacter oxydans* such as the tufB promoter from *Escherichia coli*, the tufB promoter from *Gluconobacter oxydans*, the sldh promoter from *Gluconobacter oxydans*, or the sndh promoter from *Gluconobacter oxydans*.

The plasmid for the plasmid-based overexpression system can be any plasmid that is capable of replicating in both *Escherichia coli* and *Gluconobacter oxydans* and which can be transferred between the two species. The plasmid may conveniently contain a selectable marker such that the transfer of such a plasmid can be monitored e.g. antibiotic-resistance marker, complementing marker for auxotrophy. Such a plasmid can include, but is not limited to, pVK100, pGE1, pBBR1MCS-2, RSF1010 and their derivatives (vectors with catalog numbers or information source, pVK100=ATCC 37156, pGE1=J. Ferment Bioeng. 79, 95, 1995, pBBR1MCS-2=NCCB 3434, RSF1010=NCCB 3110).

The entire SMS 37 gene was amplified by PCR using primer pair PsndhSMS 37+1 (SEQ ID NO:5) containing complementary $P_{sndh}$ promoter overhang sequence at the 5'-end and SMS 37HindIII-1 [SEQ ID NO:4 with GAGAAAGCTT at the 5'-end]. The $P_{sndh}$ promoter (SEQ ID NO:6) was amplified by PCR using primers PsndhXhoI+1 (SEQ ID NO:7) and SMS 37Psndh-1 (SEQ ID NO:8) containing complementary SMS 37 DNA overhang sequence at 5'-end. *G. oxydans* DSM 17078 genomic DNA was used as a template and the reaction conditions consisted of 35 cycles of denaturation at 94° C. for 30 sec, annealing at 50° C. for 30 sec and extension at 72° C. for 1 min. In both cases, the GC-rich PCR kit (Roche Molecular Biochemicals) was used. As the two fragments have complementary overhangs, the individual PCR fragments were mixed and re-amplified using the primer pair PsndhXhoI+1/SMS 37HindIII-1 to amplify a full length product whereby the chosen promoter was inserted upstream of the SMS 37 gene. The PCR reaction conditions for the second round reaction consisted of 94° C., 2 min, then 10 cycles of [94° C., 30 sec, 63° C., 30 sec, 68° C., 6 min], followed by 20 cycles of [94° C., 30 sec, 63° C., 30 sec, 68° C., 6 min with an additional 20 sec per cycle] and a final extension at 68° C. for 10 min. The PCR product was purified and doubly-digested with XhoI and Hindu and cloned into XhoI-HindIII-digested pVK100 vector. The ligation mix was transformed into *E. coli* TOP 10 cells and transformants were selected for on Luria-Bertani agar containing tetracycline to a final concentration of 10 μg $ml^{-1}$. Putative transformants were screened by colony PCR using primer pair PsndhXhoI+1/SMS 37HindIII-1. Positive transformants were picked, plasmid minipreps made and the DNA sequence of the insertion fragment was confirmed. Plasmids showing the correct sequence were transformed into competent *G. oxydans* DSM 17078 cells selecting transformants on mannitol broth agar medium containing tetracycline to a final concentration of 10 μg $ml^{-1}$. Several putative transformants were observed of which four were analyzed by PCR using primer pair PsndhXhoI+1/SMS 37HindIII-1 to verify the presence of the plasmid. All strains were found to contain the SMS 37 overexpression plasmid and were named *G. oxydans* DSM 17078-SMS 37up1, *G. oxydans* DSM 17078-SMS 37up2, *G. oxydans* DSM 17078-SMS 37up3 and *G. oxydans* DSM 17078-SMS 37up4.

Example 3

Production of Vitamin C from D-Sorbitol Using Resting Cells

Cells of *G. oxydans* DSM 17078, *G. oxydans* DSM 17078-SMS 37up1, *G. oxydans* DSM 17078-SMS 37up2, *G. oxydans* DSM 17078-SMS 37up3 and *G. oxydans* DSM 17078-SMS 37up4 were grown at 27° C. for 3 days on No. 3BD agar medium containing 70 g/l D-sorbitol, 0.5 g/l glycerol, 7.5 g/l yeast extract (Difco), 2.5 g/l $MgSO_4.7H_2O$, 10 g/l $CaCO_3$ and 18 g/l agar (Difco).

Cells were scraped from the agar plates, suspended in distilled water and used for resting cell reactions conducted at 30° C. with shaking at 220 rpm. A series of reactions (0.5 ml reaction mixture in 5 ml reaction tubes) was carried out with 2% D-sorbitol in reaction mixtures further containing 0.3% NaCl, 1% $CaCO_3$ and was incubated with cells at a final concentration of $OD_{600}$=10. After an incubation period of 20 hours, samples of the reaction mixtures were analyzed by high performance liquid chromatography (HPLC) using an Agilent 1100 HPLC system (Agilent Technologies, Wilmington, USA) with a LiChrospher-100-RP18 (125×4.6 mm) column (Merck, Darmstadt, Germany) attached to an Aminex-HPX-78H (300×7.8 mm) column (Biorad, Reinach, Switzerland). The mobile phase was 0.004 M sulfuric acid, and the flow rate was 0.6 ml/min. Two signals were recorded using an UV detector (wavelength 254 nm) in combination with a refractive index detector. In addition, the identification of the L-ascorbic acid was done using an amino-column (YMC-Pack Polyamine-II, YMC, Inc., Kyoto, Japan) with UV detection at 254 nm. The mobile phase was 50 mM $NH_4H_2PO_4$ and acetonitrile (40:60).

An Agilent Series 1100 HPLC-mass spectrometry (MS) system was used to identify L-ascorbic acid. The MS was operated in positive ion mode using the electrospray interface. The separation was carried out using a LUNA-C8(2) column (100×4.6 mm) (Phenomenex, Torrance, USA). The mobile phase was a mixture of 0.1% formic acid and methanol (96:4). L-Ascorbic acid eluted with a retention time of 3.1 minutes. The identity of the L-ascorbic acid was confirmed by retention time and the molecular mass of the compound.

The supernatants of the reaction mixtures incubated with cells of mutant strains *G. oxydans* DSM 17078-SMS 37up1, *G. oxydans* DSM 17078-SMS 37up2, *G. oxydans* DSM 17078-SMS 37up3 and *G. oxydans* DSM 17078-SMS 37up4 contained an average of 2.8 g/l of Vitamin C compared to 1.0 g/l for *G. oxydans* DSM 17078.

Example 4

Presence of the SMS 37 Gene and Equivalents in Other Organisms

The presence of SEQ ID NO:1 and/or equivalents in other organisms than the ones disclosed herein before, e.g. organisms as mentioned in Table 1, may be determined by a simple DNA hybridization experiment.

Strains of *Acetobacter aceti* subsp. *xylinum* IFO 13693 and IFO 13773 are grown at 27° C. for 3 days on No. 350 medium containing 5 g/l Bactopeptone (Difco), 5 g/l yeast extract (Difco), 5 g/l glucose, 5 g/l mannitol, 1 g/l $MgSO_4.7H_2O$, 5 ml/l ethanol, and 15 g/l agar. All other *Acetobacter, Gluconacetobacter* and all *Gluconobacter* strains are grown at 27° C. for 3 days on mannitol broth (MB) agar medium containing 25 g/l mannitol, 5 g/l yeast extract (Difco), 3 g/l Bactopeptone (Difco), and 18 g/l agar (Difco). *E. coli* K-12 is grown on Luria Broth agar medium. The other strains are grown on medium recommended by the suppliers or according to methods known in the art. Genomic DNA is extracted as described by e.g. Sambrook et al., 1989, "Molecular Cloning: A Laboratory Manual/Second Edition", Cold Spring Harbor Laboratory Press) from a suitable organism as, e.g. mentioned in Table 1.

Genomic DNA preparations are digested with restriction enzymes such as EcoRI or HindIII, and 1 μg of the DNA fragments are separated by agarose gel electrophoresis (1% agarose). The gel is treated with 0.25 N HCl for 15 min and then 0.5 N NaOH for 30 min, and then blotted onto nitrocellulose or a nylon membrane with Vacuum Blotter Model 785 (BIO-RAD Laboratories AG, Switzerland) according to the instruction of the supplier. The resulting blot is then brought into contact/hybridized with a solution wherein the probe, such as e.g. a DNA fragment with SEQ ID NO:1 sequence or a DNA fragment containing the part or whole of the SEQ ID NO:1 sequence to detect positive DNA fragment(s) from a test organism. A DIG-labeled probe, e.g. SEQ ID NO:1, may be prepared according to Example 1 by using the PCR-DIG labeling kit (Roche Diagnostics) and a set of primers, SEQ ID NO:3 and SEQ ID NO:4. A result of such a blot is depicted in Table 1.

The hybridization may be performed under stringent or highly stringent conditions. A preferred, non-limiting example of such conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C. Highly stringent conditions include, for example, 2 h to 4 days incubation at 42° C. in a solution such as DigEasyHyb solution (Roche Diagnostics GmbH) with or without 100 μg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 min in 2×SSC and 0.1% SDS at room temperature and then washing twice for 15-30 min in 0.5×SSC and 0.1% SDS or 0.1×SSC and 0.1% SDS at 65-68° C. To detect DNA fragments with lower identity to the probe DNA, final washing steps can be done at lower temperatures such as 50-65° C. and for shorter washing time such as 1-15 min.

The genes corresponding to the positive signals within the respective organisms shown in Table 1 can be cloned by a PCR method well known in the art using genomic DNA of such an organism together with a suitable primer set, such as e.g. SEQ ID NO:3 and SEQ ID NO:4 under conditions as described in Example 1 or as follows: 5 to 100 ng of genomic DNA is used per reaction (total volume 50 μl). Expand High Fidelity PCR system (Roche Diagnostics) can be used with reaction conditions consisting of 94° C. for 2 min; 30 cycles of (i) denaturation step at 94° C. for 15 sec, (ii) annealing step at 60° C. for 30 sec, (iii) synthesis step at 72° C. for 0.5 to 5 min depending to the target DNA length (1 min/1 kb); extension at 72° C. for 7 min. Alternatively, one can perform a PCR with degenerate primers, which can be synthesized based on SEQ ID NO:2 or amino acid sequences as consensus sequences selected by aligning several amino acid sequences obtained by a sequence search program such as BLASTP (or BLASTX when nucleotide sequence is used as a "query sequence") to find proteins having a similarity to the protein of SEQ ID NO:2. For PCR using degenerate primers, temperature of the second annealing step (see above) can be lowered to 55° C., or even to 50-45° C. A result of such an experiment is shown in Table 1.

Samples of the PCR reactions are separated by agarose gel electrophoresis and the bands are visualized with a transilluminator after staining with e.g. ethidium bromide, isolated from the gel and the correct sequence is confirmed.

Consensus sequences mentioned above might be amino acid sequences belonging to certain categories of several protein domain/family databases such as PROSITE (database of protein families and domains), COGs (Cluster of Ortholog Groups), CDD (Conserved Domain Databases), pfam (large collection of multiple sequence alignments and hidden Markov models covering many common protein domains and families). Once one can select certain protein with identical/similar function to the protein of this invention from proteins containing domain or family of such databases, corresponding DNA encoding the protein can be amplified by PCR using the protein sequence or its nucleotide sequence when it is available in public databases. Following organisms may further provide genes, which can be used as an alternative gene of this invention: *Shigella flexneri* 2a strain 301, *Salmonella typhimurium* LT2, *Bacillus subtilis* 168, *Agrobacterium tumefaciens* C58, *Bradyrhizobium japonicum* USDA 110, *Sinorhizobium meliloti* 1021 or *Mesorhizobium loci* MAFF303099.

Example 5

Overexpression of the SMS 37 Gene and Equivalents from Other Organisms for Production of Vitamin C In order to improve Vitamin C production in a suitable microorganism which is capable to directly produce Vitamin C from a given substrate, the SMS 37 gene and equivalents as, e.g. a PCR product obtained in Example 4, referred to herein as gene X, can be used in an overexpression system according to Example 2 or can be cloned into pCR2.1-TOPO (Invitrogen, Carlsbad, Calif., USA) and used to transform *E. coli* TG1 to have a $Ap^r$ transformant carrying pCR2.1-TOPO-gene X, i.e. carrying a PCR product obtained in Example 4. The insert is amplified with a set of primers, PfNdeI [SEQ ID NO:3 with CCCAT at the 5'-end] and PrHindIII [SEQ ID NO:4 with CCAAGCTT at the 5'-end], by PCR. Resulting PCR product is digested with NdeI and HindIII and the fragment is inserted together with PcrtE-SD (Shine-Dalgarno) fragment (WO 02/099095) digested with XhoI and NdeI into pVK100 (ATCC 37156) between the sites of XhoI and HindIII. *E. coli* TG1 is transformed with the ligation product to have Tc' transformant carrying plasmid pVK-PcrtE-SD-gene X, which is then used to transform a suitable host, e.g. *G. oxydans* DSM 17078 by electroporation to have e.g. Ter *G. oxydans* DSM 17078/pVK-PcrtE-SD-gene X.

Production of Vitamin C using the recombinant cells of e.g. *G. oxydans* strains DSM 17078 and the corresponding wild-type strain are performed according to Example 3.

In the resting cell reaction with 1% L-sorbosone as the substrate, the recombinant cells can produce at least more than 20% Vitamin C compared to the wild-type strain.

TABLE 1

Equivalents of the SMS 37 gene in other organisms.

| Strain | Signal 1 | Signal 2 | Signal 3 |
|---|---|---|---|
| *G. oxydans* DSM 17078 | ++++ | + | + |
| *G. oxydans* IFO 3293 | ++++ | + | + |
| *G. oxydans* IFO 3292 | ++++ | + | + |
| *G. oxydans* ATCC 621H | ++ | + | + |
| *G. oxydans* IFO 12528 | ++ | + | + |
| *G. oxydans* G 624 | + | − | + |
| *G. oxydans* T-100 | ++++ | + | + |
| *G. oxydans* IFO 3291 | + | − | + |
| *G. oxydans* IFO 3255 | + | − | + |
| *G. oxydans* ATCC 9937 | + | − | + |
| *G. oxydans* IFO 3244 | + | − | + |
| *G. cerinus* IFO 3266 | + | − | + |
| *G. frateurii* IFO 3260 | + | − | + |
| *G. oxydans* IFO 3287 | + | − | + |
| *Acetobacter aceti subsp. orleanus* IFO 3259 | − | − | + |
| *Acetobacter aceti subsp. xylinum* IFO 13693 | − | − | + |
| *Acetobacter aceti subsp. xylinum* IFO 13773 | − | − | + |
| *Acetobacter sp.* ATCC 15164 | − | − | + |
| *G. thailandicus* NBRC 100600 | + | − | + |
| *Gluconacetobacter liquefaciens* ATCC 14835 | ++ | − | + |
| *Gluconacetobacter polyoxogenes* NBI 1028 | + | − | + |
| *Gluconacetobacter diazotrophicus* ATCC 49037 | − | − | + |
| *Gluconacetobacter europaeus* DSM 6160 | − | − | + |
| *Acetobacter aceti* 1023 | − | − | + |
| *Acetobacter pasteurianus* NCI 1193 | − | − | + |
| *E. coli* | − | − | − |
| *Saccharomyces cerevisiae* | − | − | − |
| *Aspergillus niger* | − | − | − |
| Mouse | − | − | − |

Signal 1: Detection of DNA on a blot with genomic DNA of different strains and SEQ ID NO: 1 as labeled probe.
Signal 2: Detection of DNA of different strains in a PCR reaction using primer pair SEQ ID NO: 3 and SEQ ID NO: 4.
Signal 3: Detection of DNA of different strains in a PCR reaction using degenerate primers. For more explanation refer to the text.

We claim:

1. A method for the production of Vitamin C, said method comprising (a) culturing a recombinant *Gluconobacter oxydans* in an aqueous medium under conditions that allow direct production of Vitamin C from D-sorbitol or L-sorbose, wherein the recombinant *Gluconobacter oxydans* has been transformed with an isolated polynucleotide operably linked to at least one expression control sequence, wherein the polynucleotide is selected from the group consisting of : (i) a nucleotide sequence encoding the polypeptide as set forth in SEQ ID NO:2; and (ii) the nucleotide sequence set forth in SEQ ID NO:1; and wherein said polynucleotide is overexpressed in said *Gluconobacter oxydan*; and (b) isolating Vitamin C as product of said culturing; wherein at least 2.8 times more vitamin C is produced as compared to a wild type *Gluconobacter oxydans* that do not overexpress said polynucleotide.

2. The process according to claim 1, wherein the *Gluconobacter oxydans* is capable of directly producing Vitamin C from D-sorbitol in quantities of 300 mg/l or more when measured in a resting cell method after an incubation period of 20 hours.

3. The process according to claim 1, wherein the *Gluconobacter oxydans* is capable of directly producing Vitamin C from L-sorbose in quantities of 800 mg/l or more.

4. The process according to claim 1, wherein said *Gluconobacter oxydans* is *Gluconobacter oxydans* DSM 17078.

* * * * *